US008563313B2

(12) United States Patent
Srikumaran et al.

(10) Patent No.: US 8,563,313 B2
(45) Date of Patent: Oct. 22, 2013

(54) MACROPHAGE CELL-LINES FOR PROPAGATION OF PORCINE REPRODUCTIVE AND RESPIRATORY SYNDROME VIRUS

(75) Inventors: Subramaniam Srikumaran, Pullman, WA (US); Weiguo Liu, Ewa Beach, HI (US); Sudarvili Shanthalingam, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 186 days.

(21) Appl. No.: 12/526,778

(22) PCT Filed: Feb. 13, 2008

(86) PCT No.: PCT/US2008/053887
§ 371 (c)(1),
(2), (4) Date: Jan. 27, 2010

(87) PCT Pub. No.: WO2008/109237
PCT Pub. Date: Sep. 12, 2008

(65) Prior Publication Data
US 2010/0146653 A1    Jun. 10, 2010

Related U.S. Application Data

(60) Provisional application No. 60/889,583, filed on Feb. 13, 2007.

(51) Int. Cl.
| C12N 15/00 | (2006.01) |
| C12N 5/00 | (2006.01) |
| C12N 5/02 | (2006.01) |
| A01N 63/00 | (2006.01) |
| A61K 48/00 | (2006.01) |

(52) U.S. Cl.
USPC .......................... 435/455; 435/325; 424/93.21

(58) Field of Classification Search
USPC ................................ 435/455, 325; 424/93.21
See application file for complete search history.

(56) References Cited

U.S. PATENT DOCUMENTS

| 5,476,778 A | 12/1995 | Chladek |
| 5,661,012 A * | 8/1997 | Sano et al. .................... 435/115 |
| 5,840,563 A | 11/1998 | Chladek |
| 5,846,805 A | 12/1998 | Collins |
| 5,989,563 A | 11/1999 | Chladek |
| 6,042,830 A | 3/2000 | Chladek |
| 6,498,008 B2 | 12/2002 | Collins |
| 7,563,881 B2 | 7/2009 | Pensaert |
| 2006/0062788 A1 | 3/2006 | Bucala |
| 2006/0110762 A1 | 5/2006 | Kapil |

FOREIGN PATENT DOCUMENTS

| WO | WO 03/010200 | * 6/2003 |
| WO | WO 2008/109237 | 9/2008 |

OTHER PUBLICATIONS

Martin et al., 1998, Virology, 241: 101-111.*
Liu et al., 2005 [retrieved on Jul. 25, 2011]. Retrieved from the internet: URL:<http://www.ncbi.nlm.nih.gov/protein/76800610?report=genbank&log$=prottop&blast_rank=1&RID=2V70KAK701N>, pp. 1-2.*
Delputte et al., 2004, Journal of Virology, 78: 8094-8101.*
Blast Search of DQ176853.1, accessed online at http://blast.ncbi.nlm.nih.gov/ Blast.cgi, on Jan. 3, 2013.*
"Macrophage cell-lines for in vitro propagation of porcine reproductive and respiratory syndrome virus," accessed online at www.pork.org on Jan. 1, 2013.*
Crocker et al., "Molecular analysis of sialoside binding to sialoadhesin by NMR and site-directed mutagenesis," Biochemical Journal, 1999, pp. 355-361, vol. 341.
Delputte et al., "Porcine Arterivirus Attachment to the Macrophage-Specific Receptor Sialoadhesin Is Depenedent on the Sialic Acid-Binding Activity of the N-Terminal Immunoglobulin Domain of Dialoadhesin," Journal of Virology, 2007, pp. 9546-9550, vol. 81.
May et al., "Expression, crystallization, and preliminary X-ray analysis of a sialic acid-binding fragment of sialoadhesin in the presence and absence of ligand," Protein Science, 1997, pp. 717-721, vol. 6.
Nath et al., "The Amino-terminal Immunoglobulin-like Domain of Sialoadhesin Contains the Sialic Acid Binding Site," The Journal of Biological Chemistry, 1995, pp. 26184-26191, vol. 270.
Vanderheijden et al., "Involvement of Sialoadhesin in Entry of Porcine Reproductive and Respiratory Syndrome Virus into Porcine Avelolar Macrophages," Journal of Virology, 2003, pp. 8207-8215, vol. 77.
Vinson et al., "Characterization of the Sialic Acid-binding Site in Sialoadhesin by Site-directed Mutagenesis," The Journal of Biological Chemistry, 1996, pp. 9267-9272, vol. 271.
U.S. Appl. No. 60/889,583, filed Feb. 13, 2007, entitled "Macrophage Cell-Lines for In Vitro Propagation of Porcine Reproductive and Respiratory Syndrome Virus," first inventor Subramaniam Srikumaran.

* cited by examiner

*Primary Examiner* — Thaian N Ton
(74) *Attorney, Agent, or Firm* — Barry L. Davidson; Davis Wright Tremaine LLP

(57) ABSTRACT

Particular aspects provide novel recombinant cells and cell lines (e.g., macrophage cell lines) that are permissive for propagation of porcine reproductive and respiratory syndrome virus (PRRSV) propagation in vitro or in vivo. In certain aspects, novel nucleic acid sequences encoding porcine sialoadhesin were transfected into existing macrophage cell-lines from other species, rendering them permissive to PRRSV infection, and suitable for propagation of PRRSV. Particular aspects provide exemplary recombinant cloned cell lines that support the replication of PRRSV, with an obtainable PRRSV titre of between $2\times10^5$/ml and $2\times10^6$/ml. Additional aspects provide novel nucleic acid sequences and polymorphisms thereof that encode for porcine sialoadhesin. Further aspects provide PRRSV propagation and preparation methods using the novel recombinant cell lines, and methods for PRRSV antigen and vaccine production using same. Yet further aspect provide transgenic, chimerical or engrafted animals having cell comprising nucleic acid sequences encoding porcine sialoadhesin.

20 Claims, 4 Drawing Sheets

MACROPHAGE CELL-LINES FOR PROPAGATION OF PORCINE REPRODUCTIVE AND RESPIRATORY SYNDROME VIRUS

CROSS-REFERENCE TO RELATED APPLICATIONS

This application is the United States nationalization, under 35 U.S.C. §371, of International Application No. PCT/US2008/053887, filed Feb. 13, 2008, and claims the benefit of priority to U.S. Provisional Patent Application Ser. No. 60/889,583, filed Feb. 13, 2007, which are incorporated by reference herein in their entirety.

FIELD OF THE INVENTION

Aspects of the present invention relate generally to porcine viruses (e.g., porcine reproductive and respiratory syndrome virus (PRRSV)), propagation of such viruses and viral antigen or vaccine production, and in particular aspects to novel nucleic acids encoding porcine sialoadhesin and to recombinant mouse cells (e.g., macrophage cell lines) transfected with said nucleic acids that are permissive for infection and propagation of PRRSV.

BACKGROUND

Porcine Reproductive & Respiratory Syndrome Virus. Porcine reproductive and respiratory syndrome virus (PRRSV) is a positive-strand RNA virus that belongs to the Arteriviridae family. The PRRSV genomic RNA is approximately 15 kb comprising multiple open reading frames ("ORFs") encoding the RNA replicase (ORF1a and ORF1b), the glycoproteins GP2 to GP5, the integral membrane protein M, and the nucleocapsid protein N (ORFs 2 to 7). Exemplary strains are the North American and European PRRSV strains represented by the prototype VR-2332 and Lelystad virus (LV) strains, respectively (Nelsen et al., *J. Virol.* 73:270-280, 1999).

Porcine reproductive and respiratory syndrome. PRRSV and porcine parvovirus (PPV) are the most common viral causes of porcine reproductive failure (Mengeling et al., *Anim. Reprod. Sci.* 60-61:199-210, 2000). PRRSV causes porcine reproductive and respiratory syndrome ("PRRS"; variously referred to as "mystery swine disease," "swine infertility and respiratory syndrome," "porcine epidemic abortion and respiratory syndrome," abortus blauw" and "blue ear disease"), which is a major problem to the swine industry worldwide (Meng, *Vet. Microbiol.* 74:309-29, 2000). The respiratory form of the disease exhibits clinical signs which are most pronounced in piglets of 3-8 weeks in age, but are reported to occur in pigs of all ages in infected herds. The diseased piglets grow slowly, have roughened hair coats, respiratory distress (e.g., respiratory dyspnea or "thumping") and increased mortality (up to about 80% pre-weaning mortality).

PRRS is associated with both gastrointestinal and systemic secondary infections (e.g., interstitial pneumonia, diarrhea, *Salmonella choleraesuis, Streptococcus suis, Haemophilus parasuis, Actinobacillus pleuropneumoniae*) that often overwhelm the host in advanced stages.

PRRS is also associated with 'wasting syndrome.' Pigs surviving PRRSV infection are often afflicted by retarded growth rates (i.e., "runt," or "wasting" syndrome) and require additional time on feed before becoming large enough (if ever) for slaughter, producing particularly marked and commercially devastating effects.

Epidemiologically, PRRSV infection is a communicable disease that is both epidemic and endemic. It can spread like an epidemic in naive swine populations, but appears to endemically linger in affected populations (Blaha, *Vet. Res.* 31:77-83, 2000). A typical epidemic of PRRSV-induced reproductive failure is presented as a broad spectrum of clinical features including infertility, anorexia, delayed return to estrus, abortions, pre-mature births, late-term dead fetuses, stillborn pigs, weak-born pigs, and in its most severe form, sow death. There may also be an increase in the number of mummified fetuses in the later stages of an PRRSV epidemic (Mengeling et al., supra). The initial infection of sows may go unnoticed, or may manifest itself by an impaired condition or general malaise lasting up to a few days. For example, the sows may go "off feed," and experience body temperatures either above or below normal. In the farrowing phase, the sows may exhibit depression, lethargy, pyrexia and occasional vomiting. In some affected herds, up to 75% of all piglets may be lost. The economic consequences of the disease are thus devastating.

PRRSV infects and replicates in porcine alveolar macrophages (PAMs) which are the cells of predilection in the natural host. Although, PAMs survive in culture for several days or even weeks, like other differentiated cells they eventually undergo senescence and die. Acquisition of unlimited growth in vitro is one of the characteristics that define cellular immortality.

The cell-line currently available for propagation of PRRSV in vitro is the green monkey kidney cell-line (and its derivatives), which has been patented (U.S. Pat. Nos. 5,476,778; 5,840,563; 5,846,805; 5,989,563; 6,042,830; US 2001 21383 and patents and patent applications derived therefrom, both U.S. non-U.S.).

There is, therefore, a pronounced need in the art for the development of alternative cell culture systems for propagation (e.g., in vitro and in vivo propagation) of PRRSV that would provide for preparation of virus and development of efficacious vaccines based thereon, or based on epitopes thereof.

SUMMARY OF EXEMPLARY ASPECTS OF THE INVENTION

Particular aspects provide novel recombinant cells and cell lines (e.g., macrophage cell lines) that are permissive for propagation of porcine reproductive and respiratory syndrome virus (PRRSV) propagation in vitro or in vivo. In certain aspects, novel nucleic acid sequences encoding porcine sialoadhesin were transfected into existing macrophage cell-lines from other species, rendering them permissive to PRRSV infection, and suitable for propagation of PRRSV. Particular aspects provide exemplary recombinant cloned cell lines that support the replication of PRRSV, with an obtainable PRRSV titre of between $2\times10^5$/ml and $2\times10^6$/ml. Additional aspects provide novel nucleic acid sequences and polymorphisms thereof that encode for porcine sialoadhesin. Further aspects provide PRRSV propagation and preparation methods using the novel recombinant cell lines, and methods for PRRSV antigen and vaccine production using same. Yet further aspect provide transgenic, chimerical or engrafted animals having cell comprising nucleic acid sequences encoding porcine sialoadhesin.

Particular aspects provide a recombinant cell (e.g., macrophage cell) comprising a transfected nucleic acid that encodes a cell-surface porcine sialoadhesin receptor or portion thereof, the cell-surface receptor or portion thereof sufficient to provide for PRRSV binding, endocytosis, or susceptibility to PRRSV infection. In certain embodiments, the cell-surface porcine sialoadhesin receptor comprises a sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In particular implementations, the nucleic acid comprises a sequence selected from the group consisting of SEQ ID NO:1, SEQ ID NO:3, a sequence having at least 95%, 96%, 97%, 98% or 99% sequence identity with SEQ ID NOS:1 or 3, and portions thereof. In particular embodiments, the transfected nucleic acid that encodes a polypeptide comprising a sequence selected from the group consisting of SEQ ID NO:2, a sequence having greater than 99% sequence identity with SEQ ID NO:2, and PRRSV-binding portions thereof. In certain aspects, the cell is that of a macrophage cell line. In particular embodiments, the nucleic acid comprises a sequence selected from the group consisting of SEQ ID NO:1, a sequence having greater than 99% sequence identity with SEQ ID NO:1. and portions thereof. In particular embodiments, the transfected nucleic acid comprises a cDNA and/or and expression vector. In particular embodiments, the macrophage cell line is heterologous, being other than porcine. In preferred embodiments, the macrophage cell line is murine.

Further aspects provide a method for propagating PRRSV, comprising: obtaining recombinant macrophage cells comprising a transfected nucleic acid that encodes a cell-surface porcine sialoadhesin receptor or portion thereof, the cell-surface receptor or portion thereof sufficient to provide for PRRSV binding, endocystosis or susceptibility to PRRSV infection; and inoculating the cells with PRRSV, wherein PRRSV infection and propagation is afforded. In certain implementations, the method further comprises: isolating the propatated PRRSV; and preparing a PRRSV antigen or vaccine based on the isolated PRRSV, or on an epitope thereof. In certain embodiments of the methods, the cell-surface porcine sialoadhesin receptor comprises a sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In preferred aspects, the cell-surface porcine sialoadhesin receptor comprises a sequence selected from the group consisting of SEQ ID NO:2, a sequence having greater than 99% sequence identity with SEQ ID NO:2, and PRRSV-binding portions thereof. In particular embodiments, the nucleic acid comprises a sequence selected from the group consisting of SEQ ID NO:1, SEQ ID NO:3, a sequence having at least 95%, 96%, 97%, 98% or 99% sequence identity with SEQ ID NOS:1 or 3, and portions thereof. In preferred aspects, the nucleic acid comprises SEQ ID NO:1 or a sequence having greater than 99% sequence identity with SEQ ID NO:1, or a portion thereof. In certain implementations, the transfected nucleic acid comprises a cDNA and/or an expression vector. In preferred aspects the macrophage cells are that of a macrophage cell line. In certain embodiments, the macrophage cell line is heterologous, being other than porcine. Preferably, the macrophage cell line is murine. In particular implementations, at least one of inoculating and propagating of PRRSV is in vitro. In alternate implementations, at least one of inoculating and propagating of PRRSV is in vivo, wherein at least one of inoculating and propagating of PRRSV comprises use of a transgenic animal or an engrafted animal comprising recombinant macrophage cells that encode a cell-surface porcine sialoadhesin receptor, the cell-surface receptor sufficient to provide for PRRSV binding, endocytosis or susceptibility to PRRSV infection. Preferably, the transgenic or engrafted animal is a mouse.

Yet additional aspects, provide an isolated nucleic acid comprising a sequence that encodes a polypeptide comprising an amino acid sequence selected from the group consisting of SEQ ID NO:2, a sequence having greater than 99% sequence identity with SEQ ID NO:2, and PRRSV-binding portions thereof. In certain embodiments, the isolated nucleic acid comprises a sequence selected from the group consisting of SEQ ID NO:1, a sequence having greater than 99% sequence identity with SEQ ID NO:1, and portions thereof.

Yet further aspects provide a recombinant expression system, comprising an expression vector into which is inserted a nucleic acid that encodes a polypeptide comprising an amino acid sequence selected from the group consisting of SEQ ID NO:2, a sequence having greater than 99% sequence identity with SEQ ID NO:2, and PRRSV-binding portions thereof. In certain embodiments, the nucleic acid comprises a sequence selected from the group consisting of SEQ ID NO:1, a sequence having greater than 99% sequence identity with SEQ ID NO:1, and portions thereof. In particular aspects of the recombinant expression system, the nucleic acid molecule is heterologous to the expression vector. In particular aspects of the recombinant expression system, the nucleic acid molecule is inserted into said vector in proper sense orientation and correct reading frame.

Further aspects provide a non-human transgenic or chimeric animal, harboring a nucleic acid transgene that encodes a polypeptide comprising an amino acid sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In certain embodiments, the nucleic acid transgene encodes a polypeptide comprising an amino acid sequence selected from the group consisting of SEQ ID NO:2, a sequence having greater than 99% sequence identity with SEQ ID NO:2, and PRRSV-binding portions thereof. Preferably, the nucleic acid comprises a sequence selected from the group consisting of SEQ ID NO:1, a sequence having greater than 99% sequence identity with SEQ ID NO:1, and portions thereof. Preferably, the animal is a transgenic rodent, and more preferably a transgenic mouse. In certain aspects, the transgenic mouse is homozygous for the transgene, or is heterozygous for the transgene. In certain preferred embodiments of the non-human transgenic or chimeric animal, the transgene expression is driven by a promoter suitable to promote transgene expression in macrophages and/or alveolar macrophages. Preferably the animal is a transgenic mouse, harboring a porcine sialoadhesin transgene expressed in macrophages and/or alveolar macrophages

BRIEF DESCRIPTION OF THE DRAWINGS

FIG. 1A shows transfectant clone AA9 infected with PRRSV followed by staining with the anti-nucleocapsid MAb SDOW17 followed by FITC-conjugated goat anti-mouse Ig antibodies. FIG. 1B shows transfectant clone AA9 mock-infected with no PRRSV followed by staining with the anti-nucleocapsid MAb SDOW17 followed by FITC-conjugated goat anti-mouse Ig antibodies. FIG. 1C shows transfectant clone AA9 infected with PRRSV followed by staining with control MAb.

FIG. 2A shows transfectant clone BG10 infected with PRRSV followed by staining with the anti-nucleocapsid MAb SDOW17 followed by FITC-conjugated goat anti-mouse Ig antibodies. FIG. 2B shows transfectant clone BG10 mock-infected with no PRRSV followed by staining with the anti-nucleocapsid MAb SDOW17 followed by FITC-conjugated goat anti-mouse Ig antibodies. FIG. 2C shows transfectant clone BG10 infected with PRRSV followed by staining with control MAb.

FIG. 3A shows transfectant clone BD4 infected with PRRSV followed by staining with the anti-nucleocapsid MAb SDOW17 followed by FITC-conjugated goat anti-mouse Ig antibodies. FIG. 3B shows transfectant clone BD4 mock-infected with no PRRSV followed by staining with the anti-nucleocapsid MAb SDOW17 followed by FITC-conjugated goat anti-mouse Ig antibodies. FIG. 3C shows transfectant clone BD4 infected with PRRSV followed by staining with control MAb.

FIG. 4A shows PRRSV infected MARC145 cells stained with the anti-nucleocapsid MAb SDOW17 followed by FITC-conjugated goat anti-mouse Ig antibodies. FIG. 4B shows mock-infected MARC145 cells stained with the anti-nucleocapsid MAb SDOW17 followed by FITC-conjugated goat anti-mouse Ig antibodies. FIG. 4C shows PRRSV infected MARC145 cells stained with control MAb.

DETAILED DESCRIPTION

Figure 1A:
FIGS. 1A, 1B and 1C show, according to particular exemplary aspects of the present invention, that the inventive porcine sialoadhesin transfectant clone AA9 is permissive for reproductive and respiratory syndromne virus (PRRSV) infection.

According to particular aspects, transfection of porcine sialoadhesin into cell lines (e.g., macrophage cell-lines) from other species renders them susceptible to reproductive and respiratory syndromne virus (PRRSV) infection.

In certain aspects, the cDNA for porcine sialoadhesin was cloned and sequenced (GenBank accession no. DQ176853 (SEQ ID NO:1)), and has been identified as a receptor for PRRSV (SEQ ID NO:2). Comparison of the instant sequence data with a previously published sequence (GenBank accession no. NM_214346 (SEQ ID NOS:3 and 4)) revealed 15 amino acid differences, which, according to additional aspects, represent novel polymorphisms (see TABLE 3). Particular exemplary aspects provide novel macrophage cell-lines (e.g., mouse) that are permissive for PRRSV infection and/or propagation (e.g., in vitro or in vivo). In particular aspects, a transfection technique was utilized to render existing macrophage cell-lines from other species, permissive to PRRSV infection. In exemplary embodiments, the mouse macrophage cell-line J774A.1 was transfected with a novel cDNA for porcine sialoadhesin, the transfectants labeled with a monoclonal antibody specific to sialoadhesin and subjected to fluorescence-activated cell sorting. A total of 51 single-cell clones were obtained, which expressed cell-surface porcine sialoadhesin. Seventeen of these clone demonstrated persistent cell-surface expression of porcine sialoadhesin to varying degrees, and three of these clones (AA9, BG10 and BD4) were determined to be susceptible to PRRSV infection. The clone AA9 was further tested and was determined to efficiently support PRRSV replication, with an obtainable virus titre of between $2\times10^5$ TCID$_{50}$/ml and $2\times10^6$/TCID$_{50}$/ml.

Definitions

PRRSV, as used herein, refers to porcine reproductive and respiratory syndrome virus (PRRSV), which is a positive-strand RNA virus that belongs to the Arteriviridae family. The PRRSV genomic RNA is approximately 15 kb comprising multiple open reading frames ("ORFs") encoding the RNA replicase (ORF1a and ORF1b), the glycoproteins GP2 to GP5, the integral membrane protein M, and the nucleocapsid protein N (ORFs 2 to 7). Exemplary strains are the North American and European PRRSV strains represented by the prototype VR-2332 and Lelystad virus (LV) strains, respectively (Nelsen et al., *J. Virol.* 73:270-280, 1999).

As used herein, a composition refers to any mixture. It can be a solution, a suspension, liquid, powder, a paste, aqueous, non-aqueous or any combination thereof.

As used herein, a combination refers to any association between or among two or more items. The combination can be two or more separate items, such as two compositions or two collections, can be a mixture thereof, such as a single mixture of the two or more items, or any variation thereof.

As used herein, a pharmaceutical effect refers to an effect observed upon administration of an agent intended for treatment of a disease or disorder or for amelioration of the symptoms thereof.

As used herein, treatment means any manner in which the symptoms of a condition, disorder or disease or other indication, are ameliorated or otherwise beneficially altered.

As used herein therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

In particular aspects, a therapeutic effect may also encompass prophylaxis of symptoms of a condition.

As used herein, the term "subject" refers to animals, particularly mammals.

As used herein, the phrase "associated with" or "characterized by" refers to certain biological aspects such as expression of a receptor or signaling by a receptor that occurs in the context of a disease or condition. Such biological aspects may or may not be causative or integral to the disease or condition but merely an aspect of the disease or condition.

term "epitope" refers herein, as is known in the art, to an antigenic determinant of a protein of polypeptide. An epitope could comprise 3 amino acids in a spatial conformation which is unique to the epitope. Generally an epitope consists of at least 5 such amino acids. An epitope of a polypeptide or protein antigen can be formed by contiguous or noncontiguous amino acid sequences of the antigen. A single viral protein, for example, may contain many epitopes. Additionally, a polypeptide fragment of a viral protein may contain multiple epitopes. The present invention encompasses epitopes and/or polypeptides recognized by antibodies of the present invention, along with conservative substitutions thereof, which are still recognized by the antibodies. Further truncation of these epitopes may be possible.

Novel Sialoadhesin Nucleic Acids

As described herein under Example 2 below, novel porcine sialoadhesin polymorphisms were identified. Table 3 shows a comparison of the instant sequence data SEQ ID NOS:1 and 2 (accession No. DQ176853) with previously published sequences SEQ ID NOS:3 and 4 (accession no. NM_214346), showing 15 amino acid differences, which, according to additional aspects, represent novel polymorphisms (see TABLE 3). According to additional aspects, novel sialoadhesin polymorphic sequences having at least one polymorphic residue substitution of SEQ ID NO:4 selected from the group consisting of substitution with Arg at position 547 (SEQ ID NO:7), Leu at position 552 (SEQ ID NO:8), Ser at position 579 (SEQ ID NO:9), Ala at position 583 (SEQ ID NO:10), Leu at position 839 (SEQ ID NO:11), His at position 846 (SEQ ID NO:12), Arg at position 864 (SEQ ID NO:13), Thr at position 1275 (SEQ ID NO:14), Arg at position 1381 (SEQ ID NO:15), Ala at position 1392 (SEQ ID NO:16), Ile at position 1425 (SEQ ID NO:17), Ala at position 1428 (SEQ ID NO:18), Phe at position 1468 (SEQ ID NO: 19), Met at position 1475 (SEQ ID NO:20) and His at position 1672 (SEQ ID NO:21) are provided.

TABLE 3

Novel porcine sialoadhesin polymorphisms

| Amino Acid Position No. | SEQ ID NO. 2 (Accession No. DQ176853) | SEQ ID NO. 4 (Accession No. NM_214346) |
|---|---|---|
| 547 | Arg | Leu |
| 552 | Leu | Ile |
| 579 | Ser | Asn |
| 583 | Ala | Thr |
| 839 | Leu | Ser |
| 846 | His | Arg |
| 864 | Arg | His |
| 1275 | Thr | Ala |
| 1381 | Arg | His |
| 1392 | Ala | Val |
| 1425 | Ile | Val |
| 1428 | Ala | Asp |
| 1468 | Phe | Leu |
| 1475 | Met | Ile |
| 1672 | His | Tyr |

Polynucleotides and expression vectors. Particular embodiments provide an isolated nucleic acid with a sequence comprising a transcriptional initiation region and a sequence encoding a porcine sialoadhesin (e.g., nucleic acid that encodes a polypeptide comprising SEQ ID NO:2, SEQ ID NO:4, a sequence having at least 95%, 96%, 97%, 98% or 99% sequence identity with SEQ ID NOS:2 or 4, or PRRSV-binding portions thereof, and a recombinant vector comprising this polynucleotide (e.g., expression vector). Preferably, the nucleic acid sequence encodes a porcine sialoadhesin comprising SEQ ID NO:2, or a sequence having greater than 99% sequence identity with SEQ ID NO:2, or a PRRSV-binding portion thereof. Preferably, the nucleic acid comprises SEQ ID NO:1, a sequence having greater than 99% sequence identity with SEQ ID NO:1, or a portion thereof. Preferably, the transcriptional initiation region is a strong constitutively expressed mammalian pol III- or pol II-specific promoter, or a viral promoter. An exemplary expression vector used for cloning the novel porcine sialoadhesin nucleic acids disclosed herein is the pcDNA3.1D/V5-His-TOPO mammalian expression vector (Invitrogen), to yield applicants' expression vector pWL/PS constructs.

A variety of mammalian expression vectors may be used to express recombinant porcine sialoadhesin in mammalian cells. Expression vectors provide DNA sequences that are required for the transcription of cloned DNA and, in particular instances the translation of their mRNAs in an appropriate host. Such vectors can be used to express DNA in a variety of hosts such as bacteria, blue green algae, plant cells, insect cells and animal cells. Certain vectors allow the shuttling of DNA between hosts such as bacteria-yeast or bacteria-animal cells. Particular expression vectors may contain at least one of the following: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available mammalian expression vectors which may be suitable for recombinant recombinant porcine sialoadhesin expression, include but are not limited to, pcDNA3.neo (Invitrogen), pcDNA3.1 (Invitrogen), pCI-neo (Promega), pLITMUS28, pLUMUS29, pLITMUS38 and pLITMUS39 (New England Bioloabs), pcDNAI, pcD-NAIamp (Invitrogen), pcDNA3 (Invitrogen), pMCIneo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors may be used to express recombinant porcine sialoadhesin in bacterial cells. Commercially available bacterial expression vectors which may be suitable for recombinant porcine sialoadhesin expression include, but are not limited to pCR2.1 (Invitrogen), pET11a (Novagen), lambda gt11 (Invitrogen), and pKK223-3 (Pharmacia).

In particular aspects, the term "macrophage promoter" and promoter specific or suitable for cells of macrophage derived refers to a promoter or a gene that encodes a protein endogenously produced by macrophage cells and/or cells of macrophage derived lineage. Examples of such promoters include promoters for any proteins expressed in macrophages and cells of macrophage derived lineage including CD3, CD4, the CD1 1 antigens (such as CDI I A, C1 11 B and CD 11 C), CD12, CD13, CD14, CD15, CD16, CD17, CD21, CD23, CD25, CD26, CD30, CD31, CD32, CD33, CD36, CD39, CD40, CD45RO, CD45RA, CD45RB, CD49A, CD49B, CD49D, CD49E, CD49F, CD50, CD57, CD60, CD61, CD62L, CD63, CD64, CD65, CD68, CD69, CD70, CD74, CD80, CD84, CD85, CD86, CD87, CD88, CD89, CD91, CD92, CD93, CD97, CD 101, CD 102, CD 105, CD 114, CD 115 (MCSFreceptor), CD 119, CD 121B, CD127, CD135, CD148, CD155, CD156, CD157, CD 163, proteins involved in the maintenance of homeostasis in the cell, proteins involved in cell motion including actin, cellular adhesion molecules, chemokines (RANTES, MIP 1a, MIP1p, MDC, TARK), and molecules involved in the immune system (MHC-I, MHC-11, etc.). Macrophage promoters also includes promoters of any genes encoding for any proteins expressed specifically in macrophages and/or cells of macrophage derived lineage including catalase, CD 156, M-CSFR, p73, and FcgRI. The term "macrophage-specific promoter" and/or and promoter specific for cells of macrophage derived lineage refers, in particular aspects to a promoter of a gene that encodes a protein endogenously produced exclusively by macrophage cells and/or cells of macrophage derived lineage. Examples of such promoters include promoters for proteins expressed specifically in macrophages such as catalase, CD156, M-CSFR, p73, and FcgRI. However, any promoter that provides for expression in macrophages may be used. Preferably, the promoter is a macrophage-specific promoter.

Preferred Exemplary Embodiments

Particular aspects provide a recombinant macrophage cell comprising a transfected nucleic acid that encodes a cell-surface porcine sialoadhesin receptor or portion thereof, the cell-surface receptor or portion thereof sufficient to provide for porcine reproductive and respiratory syndrome virus (PRRSV) binding, endocytosis, or susceptibility to PRRSV infection. In certain embodiments, the cell-surface porcine sialoadhesin receptor comprises a sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In particular implementations, the nucleic acid comprises a sequence selected from the group consisting of SEQ ID NO:1, SEQ ID NO:3, a sequence having at least 95%, 96%, 97%, 98% or 99% sequence identity with SEQ ID NOS:1 or 3, and portions thereof. Preferably, where a portion of the porcine sialoadhesin receptor is used, where the portion is sufficient to provide for porcine reproductive and respiratory syndrome virus (PRRSV) binding, endocytosis, or susceptibility to PRRSV infection, the portion comprises at least 50, at least 75, at least 100, at least 200, at least 500, or at least 1000 contiguous amino acids (see, US 2004 0248124, incorporated herein in its entirety).

Additional aspects, provide a recombinant cell comprising a transfected nucleic acid that encodes a polypeptide comprising a sequence selected from the group consisting of SEQ ID NO:2, a sequence having greater than 99% sequence identity with SEQ ID NO:2, and PRRSV-binding portions thereof. In certain aspects, the cell is that of a macrophage cell line.

In certain embodiments of the above methods, the nucleic acid comprises a sequence selected from the group consisting of SEQ ID NO:1, a sequence having greater than 99% sequence identity with SEQ ID NO:1. and portions thereof. In particular embodiments, the transfected nucleic acid comprises a cDNA and/or and expression vector. In particular embodiments, the macrophage cell line is heterologous, being other than porcine. In preferred embodiments, the macrophage cell line is murine.

Further aspects provide a method for propagating PRRSV, comprising: obtaining recombinant macrophage cells comprising a transfected nucleic acid that encodes a cell-surface porcine sialoadhesin receptor or portion thereof, the cell-surface receptor or portion thereof sufficient to provide for PRRSV binding, endocystosis or susceptibility to PRRSV infection; and inoculating the cells with PRRSV, wherein PRRSV infection and propagation is afforded. In certain implementations, the method further comprises: isolating the propatated PRRSV; and preparing a PRRSV antigen or vaccine based on the isolated PRRSV, or on an epitope thereof. In certain embodiments of the methods, the cell-surface porcine sialoadhesin receptor comprises a sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In preferred aspects, the cell-surface porcine sialoadhesin receptor comprises a sequence selected from the group consisting of SEQ ID NO:2, a sequence having greater than 99% sequence identity with SEQ ID NO:2, and PRRSV-binding portions thereof. In particular embodiments, the nucleic acid comprises a sequence selected from the group consisting of SEQ ID NO:1, SEQ ID NO:3, a sequence having at least 95%, 96%, 97%, 98% or 99% sequence identity with SEQ ID NOS:1 or 3, and portions thereof. In preferred aspects, the nucleic acid comprises SEQ ID NO:1 or a sequence having greater than 99% sequence identity with SEQ ID NO:1, or a portion thereof. In certain implementations, the transfected nucleic acid comprises a cDNA and/or an expression vector. In preferred aspects the macrophage cells are that of a macrophage cell line. In certain embodiments, the macrophage cell line is heterologous, being other than porcine. Preferably, the macrophage cell line is murine. In particular implementations, at least one of inoculating and propagating of PRRSV is in vitro. In alternate implementations, at least one of inoculating and propagating of PRRSV is in vivo, wherein at least one of inoculating and propagating of PRRSV comprises use of a transgenic animal or an engrafted animal comprising recombinant macrophage cells that encode a cell-surface porcine sialoadhesin receptor, the cell-surface receptor sufficient to provide for PRRSV binding, endocytosis or susceptibility to PRRSV infection. Preferably, the transgenic or engrafted animal is a mouse.

Yet additional aspects, provide an isolated nucleic acid comprising a sequence that encodes a polypeptide comprising an amino acid sequence selected from the group consisting of SEQ ID NO:2, a sequence having greater than 99% sequence identity with SEQ ID NO:2, and PRRSV-binding portions thereof. In certain embodiments, the isolated nucleic acid comprises a sequence selected from the group consisting of SEQ ID NO:1, a sequence having greater than 99% sequence identity with SEQ ID NO:1, and portions thereof.

Yet further aspects provide a recombinant expression system, comprising an expression vector into which is inserted a nucleic acid that encodes a polypeptide comprising an amino acid sequence selected from the group consisting of SEQ ID NO:2, a sequence having greater than 99% sequence identity with SEQ ID NO:2, and PRRSV-binding portions thereof. In certain embodiments, the nucleic acid comprises a sequence selected from the group consisting of SEQ ID NO:1, a sequence having greater than 99% sequence identity with SEQ ID NO:1, and portions thereof. In particular aspects of the recombinant expression system, the nucleic acid molecule is heterologous to the expression vector. In particular aspects of the recombinant expression system, the nucleic acid molecule is inserted into said vector in proper sense orientation and correct reading frame.

Particular exemplary aspects provide a non-human transgenic or chimeric animal, harboring a nucleic acid transgene that encodes a polypeptide comprising an amino acid sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In certain embodiments, the nucleic acid transgene encodes a polypeptide comprising an amino acid sequence selected from the group consisting of SEQ ID NO:2, a sequence having greater than 99% sequence identity with SEQ ID NO:2, and PRRSV-binding portions thereof. Preferably, the nucleic acid comprises a sequence selected from the group consisting of SEQ ID NO:1, a sequence having greater than 99% sequence identity with SEQ ID NO:1, and portions thereof. Preferably, the animal is a transgenic rodent, and more preferably a transgenic mouse. In certain aspects, the transgenic mouse is homozygous for the transgene, or is heterozygous for the transgene. In certain preferred embodiments of the non-human transgenic or chimeric animal, the transgene expression is driven by a promoter suitable to promote transgene expression in macrophages and/or alveolar macrophages. Preferably the animal is a transgenic mouse, harboring a porcine sialoadhesin transgene expressed in macrophages and/or alveolar macrophages Biologically Active Variants of Sialoadhesin Nucleic Acids and Proteins As used herein, a "biological activity" refers to a function of a polypeptide including but not limited to complexation, dimerization, multimerization, receptor-associated ligand binding and/or endocytosis, receptor-associated protease activity, phosphorylation, dephosphorylation, autophosphorylation, ability to form complexes with other molecules, ligand binding, catalytic or enzymatic activity, activation including auto-activation and activation of other polypeptides, inhibition or modulation of another molecule's function, stimulation or inhibition of signal transduction and/or cellular responses such as cell proliferation, migration, differentiation, and growth, degradation, membrane localization, and membrane binding. A biological activity can be assessed by assays described herein and by any suitable assays known to those of skill in the art, including, but not limited to in vitro assays, including cell-based assays, in vivo assays, including assays in animal models for particular diseases.

Preferably, the porcine sialoadhesin, or polymorphic variant thereof (e.g., SEQ ID NOS:7-21) comprises an amino acid sequence of SEQ ID NO:2 (or of SEQ ID NO:2 having from 1, to about 3, to about 5, to about 10, or to about 20 conservative amino acid substitutions), or a fragment of a sequence of SEQ ID NO:2 (or of SEQ ID NO:2 having from 1, to about 3, to about 5, to about 10, or to about 20 conservative amino acid substitutions), and wherein the polypeptide is sufficient to provide for PRRSV binding, endocystosis or susceptibility to PRRSV infection. Preferably, porcine sialoadhesin, or variant thereof, comprises a sequence of SEQ ID NO:2, or a conservative amino acid substitution variant thereof.

Functional porcine sialoadhesin, functional porcine sialoadhesin variants are those proteins that display one or more of the biological activities of porcine sialoadhesin, including but not limited to ligand binding, receptor-mediated endocytosis, receptor-meidated signal transduction, receptor activation, receptor down-regulation, etc. Variants of porcine sialoadhesin have utility for aspects of the present invention.

Variants can be naturally or non-naturally occurring. Naturally occurring variants (e.g., polymorphisms) are found in various species and comprise amino acid sequences which are substantially identical to the amino acid sequence shown in SEQ ID NO:2. Species homologs of the protein can be obtained using subgenomic polynucleotides of the invention, as described below, to make suitable probes or primers for screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants are also included here. Preferably, naturally or non-naturally occurring variants have amino acid sequences which are at least 85%, 90%, 95%, 96%, 97%, 98%, 99% or greater than 99% identical to the amino acid sequence shown in SEQ ID NOS:2. More preferably, the molecules are at least 98%, 99% or greater than 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3552-59 (1969) and adopted at 37 C.F.R.§§. 1.821-1.822, abbreviations for amino acid residues are shown in Table 2:

TABLE 2

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Praline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

Guidance in determining which amino acid residues can be substituted, inserted, or deleted without abolishing biological or immunological activity can be found using computer programs well known in the art, such as DNASTAR software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. Preferably, amino acid changes in the porcine sialoadhesin polypeptide variants are conservative amino acid changes, i.e., substitutions of similarly charged or uncharged amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant. Properties and functions of porcine sialoadhesin polypeptide protein or polypeptide variants are of the same type as a protein comprising the amino acid sequence encoded by the nucleotide sequence shown in SEQ ID NO:1, although the properties and functions of variants can differ in degree.

Variants of the porcine sialoadhesin polypeptide disclosed herein include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants. Covalent variants can be prepared by linking functionalities to groups which are found in the amino acid chain or at the N- or C-terminal residue, as is known in the art.

A subset of mutants, called muteins, is a group of polypeptides in which neutral amino acids, such as serines, are substituted for cysteine residues which do not participate in disulfide bonds. These mutants may be stable over a broader temperature range than native secreted proteins (see, e.g., Mark et al., U.S. Pat. No. 4,959,314).

It will be recognized in the art that some amino acid sequences of the porcine sialoadhesin polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of ligand binding to cell surface receptors (Ostade et al., *Nature* 361:266-268, 1993). Thus, the porcine sialoadhesin polypeptides of the present invention may include one or more amino acid substitutions, deletions or additions, either from natural mutations or human manipulation.

Amino acids in the porcine sialoadhesin polypeptides of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. Science 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given porcine sialoadhesin polypeptide will not be more than 50, 40, 30, 25, 20, 15, 10, 5 or 3.

Fusion Proteins

Fusion proteins comprising proteins or polypeptide fragments of porcine sialoadhesin polypeptide can also be constructed. Fusion proteins are useful for generating antibodies against amino acid sequences and for use in various targeting and assay systems. For example, fusion proteins can be used to identify proteins which interact with a porcine sialoadhesin polypeptide of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the amino acid sequence shown in SEQ ID NO: 2 or can be prepared from biologically active variants of SEQ ID NO: 2, such as those described above. The first protein segment can include of a full-length porcine sialoadhesin polypeptide. Other first protein segments can consist of about functional portions of SEQ ID NO:2.

The second protein segment can be a full-length protein or a polypeptide fragment. Proteins commonly used in fusion protein construction include (3-galactosidase, 13-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and virus protein fusions.

These fusions can be made, for example, by covalently linking two protein segments or by standard procedures in the art of molecular biology. Recombinant DNA methods can be used to prepare fusion proteins, for example, by making a DNA construct which comprises a coding region for the protein sequence of SEQ ID NO:2 in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Transfected Macrophage Cell Lines Expressing Porcine Sialoadhesin

As described herein under Example 3 below, the novel cDNA (SEQ ID NO:1) for sialoadhesin was transfected (e.g., in the context of an exeprssion vector such as the pcDNA3.1D/V5-His-TOPO mammalian expression vector (Invitrogen) to yield the expression vector pWL/PS) into the mouse macrophage cell-line, J774A.1. The transfectants were labeled with an antibody specific for porcine sialoadhesin, followed by sorting in a fluorescence-activated cell sorter. Fifty-one (51) single clones were obtained. Of these, 17 clones continued to express porcine sialoadhesin to varying degrees (Table 1).

According to additional aspects, other macrophage lines including but not limited to mammalian, rodent (mouse, rat, hamster, etc.), bovine, ovine, equine, porcine, human, primate, simian, etc., may be used. Preferably a suitable expression vector with a promoter appropriate to the cell type is used to generate the recombinant cell lines.

Identification of Transfectant Macrophage Cell-Lines Permissive for PRRSV Infection As described herein under Example 4 below, transfectant cell-lines that are permissive for PRRSV infection were identified. Immunofluorescence assay of transfectant cells following infection with PRRSV revealed that three of the porcine sialoadhesin transfectant cell-lines were susceptible to PRRSV infection (FIGS. 1A, 1B, 1C, 2A, 2B, 2C, 3A, 3B and 3C; see also Table 1).

Identification of Transfectant Macrophage Cell-Lines Efficient for PRRSV Propagation As described herein under Example 5 below, efficient propagation of PRRSV in AA9 cells was demonstrated. The AA9 cell-line cultured in tissue culture flasks was infected with PRRSV. Taken together, the results indicate that AA9 cells support the replication of PRRSV. These cells can be successfully used for propagation of PRRSV. Virus titers ranging from $2\times10^5$/ml to $2\times10^6$/ml can be obtained from AA9 cells. This titer is only slightly less than that obtainable from MARC145 cells.

Use of Recombinant Vectors and Transfectant Macrophage Cell-Lines for Vaccine Production As described herein under Example 5 below, PRRSV produced using the novel recombinant cells has utility for vaccine production. Vaccination of pigs against PRRSV is the most prudent and logical way of controlling this economically important disease. Production of vaccines requires large scale propagation of PRRSV in the laboratories of pharmaceutical companies. The cell-line that is currently available for propagation of PRRSV in vitro is the green monkey kidney cell-line (and its derivatives). According to additional aspects, the availability of cell-lines that are permissive for PRRSV propagation for propagation of PRRSV provides for production of efficacious vaccines against PRRSV.

"Vaccine," as used herein and in the art, refers to any type of biological agent in an administratable form capable of stimulating an immune response in an animal inoculated with the vaccine. For purposes of preferred embodiments of this invention, an inventive vaccine may comprise as the viral agent, one or more immunogenic (antigenic) components of the virus, and including polypeptide-based vaccines.

In particular embodiments, the PRRSV polypeptides provide vaccines, based on the use of one or more PRRSV antigens in vaccine compositions. Such peptide-based vaccines are well known in the art, and may contain additional antigenic and adjuvant elements. Peptide-based vaccine are advantageous over traditional vaccines for several reasons: they are substantially safer; they have a relatively long shelf-life; they have the ability to target the immune response towards specific epitopes that are not suppressive nor hazardous for the host; and they offer the possibility of preparing multi-component and multi-pathogen vaccines.

The efficacy of inventive vaccines and peptide-based vaccines is enhanced by adequate presentation of the epitopes to the immune system. Therefore, in preferred aspects, the PRRSV antigens/epitopes are coupled to, or are expressed (e.g, hydrid-gene expression) as part of, a carrier that may also offer an adjuvant function. Additional adjuvants may or may not be included in the immunization.

In particular aspects, immunizations are performed with one or more PRRSV protein or polypeptide antigens selected from the group consisting of RNA replicase (ORF1a and ORF1b), the glycoproteins GP2 to GP5, the integral membrane protein M, and the nucleocapsid protein N (ORFs 2 to 7), and epitope-bearing fragments of RNA replicase (ORF1a and ORF1b), the glycoproteins GP2 to GP5, the integral membrane protein M, and the nucleocapsid protein N (ORFs 2 to 7).

Antibodies. In particular embodiments, porcine sialoadhesin polypeptides, as described above, have utility as antigens or epitopes for developing respective antibodies (e.g., monoclonal antibodies), and compositions comprising such antibodies.

In particular embodiments, the porcine sialoadhesin protein or polypeptide antigen is selected from the group consisting of SEQ ID NOS:2, 7-21, and epitope-bearing fragments of SEQ ID NOS:2 and 7-21. In particular embodiments, immunologic assay may be used in connection with the antibodies, for example, selected from the group consisting of ELISA, immunoprecipitation, immunocytochemistry, immunoelectrophoresis, immunochemical methods, Western analysis, antigen-capture assays, two-antibody sandwich assays, binder-ligand assays, agglutination assays, complement assays, and combinations thereof. In particular embodiments, the antibody is selected from the group consisting of a single-chain antibody, a monoclonal antibody, a chimeric antibody, a humanized antibody, and a Fab fragment. In particular embodiments, a plurality of antibodies, or eptitope-binding portions thereof, are used, in each case specific for an PRRSV protein or polypeptide antigen or epitope.

Therapeutic agents. Additionally, because of the nature of the relevant specific binding interactions, antibodies and antibody-containing compositions of the present invention have therapeutic utility for treatment or prevention of PRRSV infections. The inventive antibodies and antibody compositions have utility for treating an infection, for alleviating symptoms of an infection, and/or to prevent pathogen infection. Preferably, the antibodies and antibody compositions are directed against PRRSV virus, or PRRSV proteins or polypeptides, and can be used to treat or prevent PRRSV virus infection by administration to subjects in need thereof.

Specifically, particular embodiments of the present invention provide an antibody directed against a PRRSV protein or polypeptide antigen selected from the group consisting of RNA replicase (ORF1a and ORF1b), the glycoproteins GP2 to GP5, the integral membrane protein M, and the nucleocapsid protein N (ORFs 2 to 7), and epitope-bearing fragments of RNA replicase (ORF1a and ORF1b), the glycoproteins GP2 to GP5, the integral membrane protein M, and the nucleocapsid protein N (ORFs 2 to 7).

In particular embodiments, the antibody is a monoclonal antibody, or antigen-binding portion thereof. In particular embodiments, the monoclonal antibody, or antigen-binding portion thereof, is a single-chain antibody, chimeric antibody, humanized antibody or Fab fragment.

Additional aspects provide a composition, comprising at least one of the above-described antibodies. Preferably, at least one of the antibodies forms specific immunocomplexes with PRRSV whole virions, or proteins or polypeptides associated with PRRSV virions. Preferably, the composition comprises a monoclonal antibody specific for a PRRSV protein or polypeptide antigen selected from the group consisting of RNA replicase (ORF1a and ORF1b), the glycoproteins GP2 to GP5, the integral membrane protein M, and the nucleocapsid protein N (ORFs 2 to 7), and epitope-bearing fragments of RNA replicase (ORF1a and ORF1b), the glycoproteins GP2 to GP5, the integral membrane protein M, and the nucleocapsid protein N (ORFs 2 to 7).

Yet further aspects provide a pharmaceutical composition, comprising at least one of the above-described antibodies of, along with a pharmaceutically acceptable diluent, carrier or excipient. Preferably, the composition is administered to a subject, whereby the composition prevents or inhibits PRRSV infection. In particular embodiments, the composition is administered to a subject, whereby the composition ameliorates symptoms of PRRSV infection. In particular embodiments, at least one of the antibodies of the composition forms specific immunocomplexes with PRRSV whole virions, or proteins or polypeptides associated with PRRSV virions.

Yet further aspects provide methods of treating, or of preventing PRRSV virus infection, comprising administering to a subject in need thereof, a therapeutically effective amount of at least one of the above-described antibodies, or of a pharmaceutical composition comprising at least one of the antibodies. In particular embodiments, the immunoglobulin sequences are, or substantially are, porcine immunoglobulin sequences.

Antigen and Vaccine Production

As described in detail herein under Example 6 below, vaccination of pigs against PRRSV is the most prudent and logical way of controlling this economically important disease. Production of vaccines requires large scale propagation of PRRSV in the laboratories of pharmaceutical companies. The cell-line that is currently available for propagation of PRRSV in vitro is the green monkey kidney cell-line (and its derivatives). According to additional aspects, the availability of cell-lines that are permissive for PRRSV propagation for propagation of PRRSV provides for production of efficacious vaccines against PRRSV.

Transgenic, Chimeric or Engrafted Animals

As described in detail herein under Example 7 below, in particular embodiments, there is provided a transgenic or chimeric mouse whose genome comprises a porcine sialoadhesin receptor (or portion thereof) transgene. Engrafted animals, such murine xenografts are also within the scope of the present invention, and can be produced using the disclosed recombinant cell lines using art-recognized methods.

The present invention will now be illustrated by reference to the following examples which set forth particularly advantageous embodiments. However, it should be noted that these embodiments are illustrative and are not to be construed as restricting the claimed invention in any way.

EXAMPLE 1

Materials and Methods

Materials and Methods

Isolation of *Porcine alveolar* macrophages. Porcine alveolar macrophages were obtained from the lungs of 1-2 month-old piglets following euthanasia with sodium pentabarbitol. The PAMs were obtained by infusing the lungs with 200 ml of cold sterile phosphate-buffered saline (PBS), and subjected to Ficoll-Paque density gradient centrifugation. PAMs were collected from the band at the PBS-Ficoll interface, and washed twice with ice-cold PBS.

Cloning of porcine sialoadhesin. Total RNA from PAMs was isolated using the RNeasy Mini Kit (Qiagen) according to the manufacturer's instructions. The cDNA was obtained by reverse transcription and PCR. Total RNA from PAMs was reverse-transcribed to generate the first strand cDNA with M-MLV reverse transcriptase (Promega) following manufacturer's recommendations. This cDNA was subsequently used in PCR reactions to obtain the full length Sialoadhesin coding sequence (CDS) using the following primers: forward primer 5' CACCATGGACTTCCTGCTCCTGCTCCTC (SEQ ID NO:5) and reverse primer 5' CTTGGGGTTTGAAGCTAG-GTCATAA (SEQ ID NO:6). PCR reactions were carried out in a total volume of 50 µl consisting of 2.5 µl of cDNA, 300 pM each of forward and reverse primers, 0.2 mM dNTPs, 1×Pfu buffer, 0.25 mM $MgSO_4$ and 5 U Pfu Turbo Hotstart™ Polymerase (Stratagene). DNA was denatured at 95° C. for 2 min, followed by 35 amplification cycles of 95° C. for 30 s, 64° C. for 30 s, and 72° C. for 5 min. An additional extension at 72° C. for 10 min followed. The single-band PCR amplicons were cloned into the pcDNA3.1D/V5-His-TOPO mammalian expression vector (Invitrogen), yielding the expression vector pWL/PS. Following transformation of TOP10 chemically competent cells (Invitrogen) with pWL/PS, positive clones were selected on LB-ampicillin plates, screened by PCR, and confirmed by restriction enzyme digest analysis. Four independent clones were sequenced in both directions using BigDye™ Terminator Chemistries and an ABI Prism™ 377 DNA sequencer (Applied Biosystems). The porcine PRRSV receptor sialoadhesin cDNA sequence was deposited by applicants at GenBank (accession no. DQ176853).

Alignment of nucleotide and amino acid sequences and similarity analyses were performed with ClustalW (http://dot.imgen.bcm.tmc.edu:9331/multi-align/Options/clustal-w.html), GeneDoc v.2.6.002 (Nicholas et al., 1997), and the Alignx™ module of Vector NTI Advance™ 9.1 (Invitrogen). Primer design was performed using Primer 3 (Rozen and Skaletsky, 2000) and Vector NTI (Invitrogen). DNA sequence analysis, fragment assembly, and amino acid sequence prediction were performed with the ContigExpress™ module of Vector NTI Advance™ 9.1 (Invitrogen) and Sequencher 4.5 (Gene Codes Corporation). SignalP v.2.0.b2 and NetNGlyc v.1.0 provided peptide signal and N-glycosylation sites prediction, respectively.

Transfection of cDNA for porcine sialoadhesin into already existing macrophage cell-lines from other species. The mouse macrophage cell line J774A.1 was used as an exemplary heterologous cell line for transfection with pWL/PS by using transfect amine 2000 (Invitrogen). Transfectants that continued to grow in the selection medium containing Geneticin were subjected to flow cytometric analysis with the monoclonal antibody, 41D3, specific for porcine sialoadhesin (kindly provided by Dr. Hans Nauwynck, Ghent University, Belgium and Michael Murtaugh, University of Minnesota, USA), followed by FITC-conjugated goat antibodies to murine Ig. Transfectants expressing sialoadhesin on their surface were sorted with a fluorescence-activated cell sorter (FACSVantage™ SE), and the sorted cells were directly transferred into 96-well microtiter culture plates at a cell concentration of one cell per well. Single clones were picked up from the individual wells of the culture plates and cultured to obtain the cell-lines.

Identification of cell-lines that are permissive for PRRSV infection. The transfectant cell-lines were tested for susceptibility to PRRSV infection. The cells cultured on chamber slides were infected with PRRSV at an moi of 5. The infectivity was determined by immunofluorescence assays with a monoclonal antibody specific for the nucleocapsid protein (SDOW17). Briefly, 48 hours post-infection, cells were fixed and permeabilized using methanol and acetone (50:50 vol/vol) at −20° C. for 10 min. The permeabilized cells were incubated with the anti-nucleocapsid mAb, SDOW17, followed by FITC-conjugated secondary antibody (goat anti-mouse Ig). The cells were then subjected to fluorescence microscopy.

Propagation of PRRSV in the transfectant cell-line AA9. AA9 cells were seeded into T25 cm² tissue culture flasks and incubated until the cells showed >70% confluence. On the day of virus infection, the spent culture medium was discarded and the cells were washed twice with DMEM medium. Virus was diluted in DMEM medium (without serum) and inoculated onto the cells at an moi of 1. Following 2 hours of incubation with intermittent rocking of the flask, complete culture medium (DMEM containing 5% fetal bovine serum, 2 mM glutamine and 20 ug/ml gentamicin) was added. The flasks were incubated at 37° C. Three days post-infection, the infected cells showed changes in morphology, and subsequently began to die. The un-infected (mock-infected) cells did not show these changes. On day 5 post-infection, the virus was harvested by subjecting the flask to repeated freeze/thaw cycles followed by centrifugation (600×g for 5 min) of the culture supernatant fluid, and stored at −80° C. until used later. This experiment was repeated 3 times.

The Titer of AA9-Propagated PRRSV was Determined by Two Methods:

1. Immunofluorescence Assay. The AA9-propagated virus was diluted ten-fold in serum-free DMEM medium. The virus was inoculated at dilutions ranging from $1\times10^{-2}$ to $1\times10^{-7}$ onto MARC145 cells grown on chamber slides. After 72 hrs, the cells were fixed in methanol:acetone (50:50) solution at −20° C. for 10 minutes and stained with anti-nucleocapsid antibody, SDOW-17 (1:200 dilution), followed by GAM-FITC (1:200 dilution), or an isotyped-matched control antibody. The stained cells were observed under a fluorescence microscope. This assay was repeated two times.

2. Reed and Muench Method. MARC145 and AA9 cells were seeded into the wells of 96 well tissue culture plates, and incubated until a confluent monolayer of cells was observed. Ten fold dilutions ($1\times10^{-2}$ to $1\times10^{-8}$) of the virus in DMEM medium (without serum) were prepared. The spent culture medium was removed from the wells, and cells were washed twice with DMEM medium. 50 μl of diluted virus was added to each well (each dilution had 5 replicates). After, two hours of incubation at 37° C. with intermittent rocking of the plates, 100 μl of complete growth medium were added to all the wells. The plates were incubated until death of cells was observed. The cells showed plaques 4 to 5 days post-inoculation of the virus. The number of wells totally affected (in each dilution) was counted, and $TCID_{50}$ was calculated. This assay was repeated three times.

EXAMPLE 2

Novel Porcine Sialoadhesin Polymorphisms were Identified

Table 3 shows a comparison of the instant sequence data SEQ ID NO:2 with a previously published sequence (GenBank accession no. NM 214346 (SEQ ID NO:3)), showing 15 amino acid differences, which, according to additional aspects, represent novel polymorphisms (see TABLE 3).

TABLE 3

Porcine Sialoadhesin Polymorphisms

| Amino Acid Position No. | SEQ ID NO. 2 (Accession No. DQ176853) | SEQ ID NO. 4 (Accession No. DQ176853) |
|---|---|---|
| 547 | Arg | Leu |
| 552 | Leu | Ile |
| 579 | Ser | Asn |
| 583 | Ala | Thr |
| 839 | Leu | Ser |
| 846 | His | Arg |
| 864 | Arg | His |
| 1275 | Thr | Ala |
| 1381 | Arg | His |
| 1392 | Ala | Val |
| 1425 | Ile | Val |
| 1428 | Ala | Asp |
| 1468 | Phe | Leu |
| 1475 | Met | Ile |
| 1672 | His | Tyr |

EXAMPLE 3

The Porcine Sialoadhesin Gene was Stably Transfected into Existing Macrophage Cell-Lines of other Species (Non-Porcine))

A novel gene, comprising novel polymorhphic amino acid positions and residues, and coding for porcine sialoadhesin was cloned as described herein. A porcine sialoadhesin sequence (SEQ ID NOS:3 and 4) was preciously as a receptor for PRRSV on PAMs. Comparison of the instant sequence data with that published in Europe revealed 15 polymmorphic amino acid differences (see above Table 3). The cDNA (SEQ ID NO:1) for sialoadhesin was transfected into the mouse macrophage cell-line, J774A.1. The transfectants were labeled with an antibody specific for porcine sialoadhesin, followed by sorting in a fluorescence-activated cell sorter. Fifty-one (51) single clones were obtained. Of these, 17 clones continued to express porcine sialoadhesin to varying degrees (Table 1).

TABLE 1

Sialoadhesin expression and PRRSV susceptibility of sialoadhesin transfectants:

| Clone Designation | Sialoadhesin Expression | PRRSV Susceptibility |
|---|---|---|
| AA9 | + | + |
| AB5 | − | |
| AB8 | − | |
| AB10 | + | − |
| AC6 | − | |
| AD3 | − | |
| AF4 | + | − |
| AF10 | − | |
| AG8 | + | − |
| AG11 | + | − |
| AH12 | − | |
| BA3 | + | − |
| BA9 | + | − |
| BC9 | − | |
| BD4 | + | + |
| BD10 | − | |
| BE6 | + | − |
| BE7 | − | |
| BF7 | − | |
| BG10 | + | + |
| CB3 | − | |
| CB6 | − | |

TABLE 1-continued

Sialoadhesin expression and PRRSV susceptibility of sialoadhesin transfectants:

| Clone Designation | Sialoadhesin Expression | PRRSV Susceptibility |
| --- | --- | --- |
| CB9 | − | |
| CC1 | − | |
| CC3 | − | |
| CD6 | + | − |
| CE9 | − | |
| CE10 | − | |
| CE11 | − | |
| CF6 | − | |
| CF8 | − | |
| CG2 | − | |
| CG5 | − | |
| CG6 | + | − |
| CG11 | − | |
| CH7 | − | |
| DA2 | − | |
| DA4 | + | − |
| DA7 | − | |
| DB1 | − | |
| DB2 | − | |
| DB7 | + | − |
| DC12 | − | |
| DD6 | + | − |
| DE5 | − | |
| DF2 | − | |
| DF5 | − | |
| DF8 | + | − |
| DF9 | + | − |
| DF10 | − | |
| DH6 | − | |

EXAMPLE 4

Transfectant Cell-Lines that are Permissive for PRRSV Infection were Identified

Immunofluorescence assay of transfectant cells following infection with PRRSV revealed that three of the porcine sialoadhesin transfectant cell-lines were susceptible to PRRSV infection (FIGS. 1A, 1B, 1C, 2A, 2B, 2C, 3A, 3B and 3C; see also Table 1).

Figure 1B:
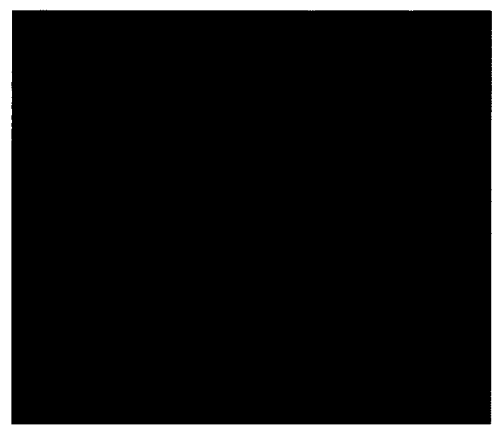
Figure 1C:
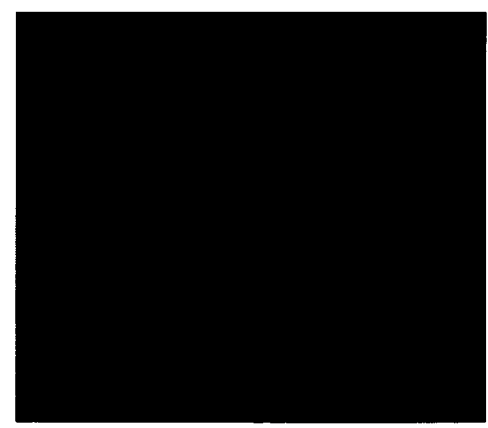

FIGS. 1A, 1B and 1C show, according to particular exemplary aspects of the present invention, that the inventive porcine sialoadhesin transfectant clone AA9 is permissive for PRRSV infection. FIG. 1A shows transfectant clone AA9 infected with PRRSV followed by staining with the anti-nucleocapsid MAb SDOW17 followed by FITC-conjugated goat anti-mouse Ig antibodies. FIG. 1B shows transfectant clone AA9 mock-infected with no PRRSV followed by staining with the anti-nucleocapsid MAb SDOW17 followed by FITC-conjugated goat anti-mouse Ig antibodies. FIG. 1C shows transfectant clone AA9 infected with PRRSV followed by staining with control MAb.

Figure 2A:
FIGS. 2A, 2B and 2C show, according to particular exemplary aspects of the present invention, that the inventive porcine sialoadhesin transfectant clone BG10 is permissive for PRRSV infection.
Figure 2B:
Figure 2C:

FIGS. 2A, 2B and 2C show, according to particular exemplary aspects of the present invention, that the inventive porcine sialoadhesin transfectant clone BG10 is permissive for PRRSV infection. FIG. 2A shows transfectant clone BG10 infected with PRRSV followed by staining with the anti-nucleocapsid MAb SDOW17 followed by FITC-conjugated goat anti-mouse Ig antibodies. FIG. 2B shows transfectant clone BG10 mock-infected with no PRRSV followed by staining with the anti-nucleocapsid MAb SDOW17 followed by FITC-conjugated goat anti-mouse Ig antibodies. FIG. 2C shows transfectant clone BG10 infected with PRRSV followed by staining with control MAb.

Figure 3A:
FIGS. 3A, 3B and 3C show, according to particular exemplary aspects of the present invention, that the inventive porcine sialoadhesin transfectant clone BD4 is permissive for PRRSV infection.
Figure 3B:
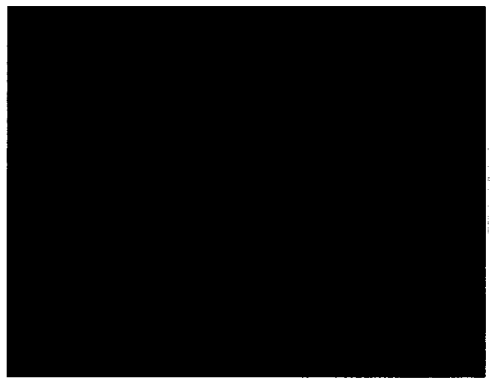
Figure 3C:
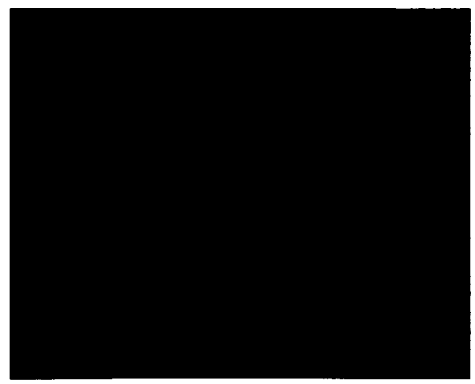

FIGS. 3A, 3B and 3C show, according to particular exemplary aspects of the present invention, that the inventive porcine sialoadhesin transfectant clone BD4 is permissive for PRRSV infection. FIG. 3A shows transfectant clone BD4 infected with PRRSV followed by staining with the anti-nucleocapsid MAb SDOW17 followed by FITC-conjugated goat anti-mouse Ig antibodies. FIG. 3B shows transfectant clone BD4 mock-infected with no PRRSV followed by staining with the anti-nucleocapsid MAb SDOW17 followed by FITC-conjugated goat anti-mouse Ig antibodies. FIG. 3C shows transfectant clone BD4 infected with PRRSV followed by staining with control MAb.

The AA9 was selected for further characterization (see Example 4 below).

EXAMPLE 5

Efficient Propagation of PRRSV in AA9 Cells was Demonstrated

The AA9 cell-line cultured in tissue culture flasks was infected with PRRSV. On day 5 post-infection, the virus was harvested and titered by two methods.

Figure 4A:
FIGS. 4A, 4B and 4C shows, according to particular exemplary aspects of the present invention, that the exemplary porcine sialoadhesin transfectant cell line AA9 is permissive for PRRSV propagation. MARC145 cells were infected with AA9-propagated PRRSV, and the virus produced in the MARC145 cells was stained with the anti-nucleocapsid MAb SDOW17, followed by FITC-conjugated goat anti-mouse Ig antibodies.
Figure 4B:
Figure 4C:

Immunofluorescence assay. The immunofluorescence assay of AA9-propagated PRRSV on MARC145 cells grown on chamber slides revealed that the MARC145 cells were infected by the AA9-propagated PRRSV up to the dilution of $1 \times 10^{-5}$ (FIGS. 4A, 4B and 4C). These results indicate that the titer of the PRRSV propagated in AA9 cells grown in tissue culture flasks was $1 \times 10^5$ per ml.

Reed and Muench Method. AA9-propagated PRRSV was also titered by the Reed and Muench Method, as described under Materials and Methods. The titering was performed on both MARC145 cells and AA9 cells. For comparison, PRRSV propagated in MARC145 cells was also titered on MARC145 cells and AA9 cells (Table 2).

TABLE 2

Determination of the titer of PRRSV propagated in AA9 cells.
One experiment representative of 5 experiments is shown.

| Virus dilution | # of infected wells (out of 5) | # of uninfected wells | Accumulative | | Ratio infected | % infected |
| --- | --- | --- | --- | --- | --- | --- |
| | | | Infected | Not infected | | |
| $10^{-2}$ | 5 | 0 | 17 | 0 | 17/17 | 100 |
| $10^{-3}$ | 5 | 0 | 12 | 0 | 12/12 | 100 |
| $10^{-4}$ | 5 | 0 | 7 | 0 | 7/7 | 100 |
| $10^{-5}$ | 2 | 3 | 2 | 3 | 2/5 | 40 |
| $10^{-6}$ | 0 | 5 | 0 | 8 | 0/8 | 0 |
| $10^{-7}$ | 0 | 5 | 0 | 13 | 0/13 | 0 |
| $10^{-8}$ | 0 | 5 | 0 | 18 | 0/18 | 0 |

The proportionate distance (PD) between the 2 dilutions ($10^{-4}$ and $10^{-5}$), where the 50% end point lies:

$$= \frac{\% \text{ infection above } 50\% - 50\%}{\% \text{ infection above } 50\% - \% \text{ infection below } 50\%}.$$

$$= \frac{100 - 50}{100 - 40} = \frac{50}{60} = 0.833$$

Exponential of dilution (ED) of exactly 50% infectivity =

$$PD \times [ED \text{ next below } 50\% - ED \text{ next above } 50\%] +$$

$$ED \text{ next above } 50\% =$$

$$0.833 \times [(-5) - (-4)] + (-4) = (-0.833) + (-4) = -4.883$$

Titer of the virus = $10^{4.833}$ $TCID_{50}/50$ ul, or $2 \times 10^{5.833}$ $TCID_{50}/ml$ The titer of the virus propagated in AA9 cells and titered on MARC145 cells in three different experiments was $2\times10^{5.8}$/ml, $2\times10^6$/ml, $2\times10^{5.6}$/ml, respectively.

The titer of the virus propagated in MARC145 cells and titered on MARC145 cells was $2\times10^{6.4}$/ml.

The titer of the virus propagated in AA9 cells and titered on AA9 cells was $2\times10^6$/ml.

The titer of the virus previously propagated in MARC145 cells and titered on AA9 cells was $2\times10^6$/ml.

Taken together, the above results clearly indicate that AA9 cells support the replication of PRRSV. These cells can be successfully used for propagation of PRRSV. Virus titers ranging from $2\times10^5$/ml to $2\times10^6$/ml can be obtained from AA9 cells. This titer is only slightly less than that obtainable from MARC145 cells.

EXAMPLE 6

PRRSV Produced using the Novel Recombinant Cells has Utility for Vaccine Production Vaccination of pigs against PRRSV is the most prudent and logical way of controlling this economically important disease. Production of vaccines requires large scale propagation of PRRSV in the laboratories of pharmaceutical companies. The cell-line that is currently available for propagation of PRRSV in vitro is the green monkey kidney cell-line (and its derivatives). According to additional aspects, the availability of cell-lines that are permissive for PRRSV propagation for propagation of PRRSV provides for production of efficacious vaccines against PRRSV.

EXAMPLE 7

Transgenic and/or Chimeric Animals Harboring)

A "transgenic animal" is an animal containing one or more cells bearing genetic information received, directly or indirectly, by deliberate genetic manipulation at a subcellular level, such as by microinjection or infection with recombinant virus. This introduced DNA molecule can be integrated within a chromosome, or it can be extra-chromosomally replicating DNA. Unless otherwise noted or understood from the context of the description of an animal, the term "transgenic animal" as used herein refers to a transgenic animal in which the genetic information was introduced into a germ line cell, thereby conferring the ability to transfer the information to offspring. If offspring in fact possess some or all of the genetic information, then they, too, are transgenic animals. The genetic information is typically provided in the form of a transgene carried by the transgenic animal.

In particular embodiments, there is provided a transgenic mouse whose genome comprises a transgene comprising a transcriptional control region operably linked to a nucleic acid (e.g., cDNA) encoding a porcine sialoadhesin receptor (or portion thereof) polypeptide comprising a sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof, or preferably comprising an amino acid sequence selected from the group consisting of SEQ ID NO:2, a sequence having greater than 99% sequence identity with SEQ ID NO:2, and PRRSV-binding portions thereof, wherein said control region comprises a promoter wherein expression of the porcine sialoadhesin receptor (or portion thereof) polypeptide at the cell surface is sufficient to provide for PRRSV binding, endocytosis, or susceptibility to PRRSV infection. In other embodiments, the nucleic acid sequence within the transgene may include sequence variations, polymorphisms, mutations and deletions, which do not abrogate the sufficiency to provide for PRRSV binding, endocytosis, or susceptibility to PRRSV infection. In certain embodiments, there is provided a transgene comprising a transcriptional control region operably linked to a nucleic acid (e.g., cDNA) encoding a porcine sialoadhesin receptor (or portion thereof) polypeptide as defined above wherein said control region comprises a promoter suitable to provide for macrophage expression of the porcine sialoadhesin receptor (or portion thereof). In particular some embodiments, the transgene may include a suitable enhancer.

In another aspect of the invention, there is provided a method for producing a transgenic mouse whose genome comprises a transgene comprising a transcriptional control region operably linked to a nucleic acid (e.g., cDNA) encoding a porcine sialoadhesin receptor (or portion thereof) polypeptide comprising a sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof, or preferably comprising an amino acid sequence selected from the group consisting of SEQ ID NO:2, a sequence having greater than 99% sequence identity with SEQ ID NO:2, and PRRSV-binding portions thereof, the method comprising: introducing into a fertilized mouse egg a transgene comprising a transcriptional control region operably linked to the nucleic acid as described above, wherein said control region comprises a promoter; transplanting the injected egg in a foster parent female mouse; and selecting a mouse derived from an injected egg whose genome comprises the transgene. As will be appreciated by one of skill in the art, the transgene may be introduced into the mouse egg by any of a number of suitable methods known in the art. Alternatively, the transgene may be introduced into embryonic stem cells (ES cells), and chimeric animals produded using the transgenic ES cells, using art recognized methods. The resulting chimeric animals are then crossed to produce the desired transgenic mice.

Engrafted animals, such murine xenografts are also within the scope of the present invention, and can be produced using the disclosed recombinant cell lines using art-recognized methods.

Particular exemplary aspects provide a non-human transgenic or chimeric animal, harboring a nucleic acid transgene that encodes a polypeptide comprising an amino acid sequence selected from the group consisting of SEQ ID NO:2, SEQ ID NO:4, a sequence having at least 95%, 96%, 97%, 98% or 99% sequence identity with SEQ ID NOS:2 or 4, and PRRSV-binding portions thereof. In certain embodiments, the nucleic acid transgene encodes a polypeptide comprising an amino acid sequence selected from the group consisting of SEQ ID NO:2, a sequence having greater than 99% sequence identity with SEQ ID NO:2, and PRRSV-binding portions thereof. Preferably, the animal is a transgenic rodent, and more preferably a transgenic mouse. In certain aspects, the transgenic mouse is homozygous for the transgene, or is heterozygous for the transgene. In certain preferred embodiments of the non-human transgenic or chimeric animal, the transgene expression is driven by a promoter suitable to promote transgene expression in macrophages and/or alveolar macrophages. Preferably the animal is a transgenic mouse, harboring a porcine sialoadhesin transgene expressed in macrophages and/or alveolar macrophages.

According to additional aspects, such transgenic or engrafted animals provide novel model systems and/or tools for studying PRRSV-mediated infection, viral propagation and disease.

Applicants have, therefore, cloned a novel polymorphic cDNA (SEQ ID NO:1) that encodes for a novel sialoadhesin polypeptide (SEQ ID NO:2), that functions, as demonstrated herein, as a PRRSV receptor. The porcine sialoadhesin cDNA sequence (SEQ ID NO:1) was transfected into a murine macrophage cell-line rendering it permissive for PRRSV propagation. Fifty-one (51) clones of transfectants were isolated and, of these, 17 clones continued to express sialoadhesin to varying degrees. Three (3) transfectant clones were identified that were susceptible to PRRSV. One of these exemplary clones, AA9, was further characterized and was found to support the replication of PRRSV. The titer of PRRSV obtainable in AA9 cells was determined to be between $2\times10^5$/ml and $2\times10^6$/ml.

These cell-lines have substantial utility as cell-lines for large scale production of PRRSV for development of vaccines against PRRSV. This present cloned gene sequences, and the transfectants expressing the sialoadhesin will also be useful for determining the mechanism by which PRRSV gets into the PAMs and causes the disease in pigs.

The invention claimed is:

1. An isolated recombinant mouse macrophage cell or recombinant mouse macrophage cell-line, comprising a transfected nucleic acid that encodes a cell-surface porcine sialoadhesin receptor or portion thereof, the cell-surface receptor or portion thereof sufficient to provide for porcine reproductive and respiratory syndrome virus (PRRSV) binding, endocytosis, and permissive PRRSV infection, wherein the cell-surface porcine sialoadhesin receptor or portion thereof comprises the first 546 amino acids of SEQ ID NO:2.

2. The recombinant mouse macrophage or cell-line of claim 1, wherein the cell-surface porcine sialoadhesin receptor comprises a sequence selected from the group consisting of SEQ ID NO:2, SEQ ID NO:4, a sequence having at least 99% sequence identity with SEQ ID NOS:2 or 4, and PRRSV-binding portions thereof, provided that the cell-surface porcine sialoadhesin receptor or portion thereof comprises the first 546 amino acids of SEQ ID NO: 2.

3. The recombinant mouse macrophage cell or cell-line of claim 1, wherein the nucleic acid comprises a sequence selected from the group consisting of SEQ ID NO:1, SEQ ID NO:3, a sequence having at least 99% sequence identity with SEQ ID NOS:1 or 3, and portions thereof encoding a PRRSV-binding portion of SEQ ID NO:2 and SEQ ID NO:4, respectively, provided that the encoded cell-surface porcine sialoadhesin receptor or portion thereof comprises the first 546 amino acids of SEQ ID NO:2.

4. The recombinant mouse macrophage cell or cell-line of claim 3, wherein the nucleic acid comprises a sequence selected from the group consisting of SEQ ID NO:1, and portions thereof encoding a PRRSV-binding portion of SEQ ID NO:2.

5. The recombinant mouse macrophage cell of claim 1, wherein the transfected nucleic acid comprises a cDNA-based expression vector.

6. The recombinant cell or cell-line of claim 1, wherein the recombinant mouse macrophage cell is based on the macrophage cell line J774A.1.

7. A method for propagating porcine reproductive and respiratory syndrome virus (PRRSV), comprising:
obtaining recombinant mouse macrophage cells comprising a transfected nucleic acid that encodes a cell-surface porcine sialoadhesin receptor or portion thereof, the cell-surface receptor or portion thereof sufficient to provide for PRRSV binding, endocytosis and permissive PRRSV infection, wherein the cell-surface porcine sialoadhesin receptor or portion thereof comprises the first 546 amino acids of SEQ ID NO:2; and
inoculating the cells with PRRSV, wherein PRRSV infection and propagation to provide for permissive infection is afforded.

8. The method of claim 7, further comprising:
isolating the propatated PRRSV; and
preparing a PRRSV antigen or vaccine based on the isolated PRRSV, or on an epitope thereof.

9. The method of claim 7, wherein the cell-surface porcine sialoadhesin receptor comprises a sequence selected from the group consisting of SEQ ID NO:2, SEQ ID NO:4, a sequence having at least 99% sequence identity with SEQ ID NOS:2 or 4, and PRRSV-binding portions thereof, provided that the cell-surface porcine sialoadhesin receptor or portion thereof comprises the first 546 amino acids of SEQ ID NO:2.

10. The method of claim 9, wherein the cell-surface porcine sialoadhesin receptor comprises a sequence selected from the group consisting of SEQ ID NO:2, a sequence having greater than 99% sequence identity with SEQ ID NO:2, and PRRSV-binding portions thereof.

11. The method of claim 7, wherein the nucleic acid comprises a sequence selected from the group consisting of SEQ ID NO:1, SEQ ID NO:3, a sequence having at least 99% sequence identity with SEQ ID NOS:1 or 3, and portions thereof encoding a PRRSV-binding portion of SEQ ID NO:2, and SEQ ID NO:4, respectively, provided that the encoded cell-surface porcine sialoadhesin receptor or portion thereof comprises the first 546 amino acids of SEQ ID NO:2.

12. The method of claim 11, wherein the nucleic acid comprises SEQ ID NO:1 or a sequence having greater than 99% sequence identity with SEQ ID NO:1, or a portion thereof encoding a PRRSV-binding portion of SEQ ID NO:2.

13. The method of claim 7, wherein the transfected nucleic acid comprises a cDNA-based expression vector.

14. The method of claim 7, wherein the recombinant cells are that of a mouse macrophage cell line.

15. The method of claim 7, wherein at least one of inoculating and propagating of PRRSV is in vitro.

16. The method of claim 7, wherein at least one of inoculating and propagating of PRRSV is in vivo.

17. The method of claim 16, wherein at least one of inoculating and propagating of PRRSV comprises use of an engrafted animal comprising engrafted recombinant mouse macrophage cells that encode the cell-surface porcine sialoadhesin receptor sufficient to provide for PRRSV binding, endocytosis and permissive PRRSV infection.

18. The method of claim 17, wherein the engrafted animal is a mouse.

19. A recombinant expression system comprising an expression vector comprising SEQ ID NO: 1 or a portion of SEQ ID NO:1 encoding a PRRSV-binding portion of SEQ ID NO:2 comprising the first 546 amino acids of SEQ ID NO:2.

20. The recombinant expression system according to claim 19, wherein the nucleic acid molecule is heterologous to the expression vector, and wherein the nucleic acid molecule is inserted into said vector in proper sense orientation and correct reading frame.

* * * * *

UNITED STATES PATENT AND TRADEMARK OFFICE
CERTIFICATE OF CORRECTION

PATENT NO. : 8,563,313 B2  Page 1 of 1
APPLICATION NO. : 12/526778
DATED : October 22, 2013
INVENTOR(S) : Srikumaran et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 273 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 6

<210> SEQ ID NO 1
<211> LENGTH: 5222
<212> TYPE: DNA
<213> ORGANISM: Sus scrofa (pig)
<220> FEATURE:
<221> NAME/KEY: CDS
<222> LOCATION: (1)...(5193)

<400> SEQUENCE: 1

```
atg gac ttc ctg ctc ctg ctc ctc ctg gct tca tct gct cta gca         48
Met Asp Phe Leu Leu Leu Leu Leu Leu Ala Ser Ser Ala Leu Ala
 1               5                  10                  15 ggc ctg gcc tcg tgg acg gtt tcc agc ccc gag acc gtg cag ggc atc     96
Gly Leu Ala Ser Trp Thr Val Ser Ser Pro Glu Thr Val Gln Gly Ile
             20                  25                  30 aag ggc tcc tgc ctc atc atc ccc tgc acc ttc ggc ttc ccg gcc aac    144
Lys Gly Ser Cys Leu Ile Ile Pro Cys Thr Phe Gly Phe Pro Ala Asn
         35                  40                  45 gtg gag gtg ccc cat ggc atc aca gcc atc tgg tac tat gac tac tca    192
Val Glu Val Pro His Gly Ile Thr Ala Ile Trp Tyr Tyr Asp Tyr Ser
     50                  55                  60 ggc aag cgc ctg gta gtg agc cac tcc agg aac cca aag gtg gtg gag    240
Gly Lys Arg Leu Val Val Ser His Ser Arg Asn Pro Lys Val Val Glu
 65                  70                  75                  80 aac cac ttc caa ggc cgg gcc ctg ctg ttg ggg cag gtt gag cag agg    288
Asn His Phe Gln Gly Arg Ala Leu Leu Leu Gly Gln Val Glu Gln Arg
                 85                  90                  95 acg tgc agc ctg ctg ctg aag gac ctg cag ccc cag gac tcg ggc tcc    336
Thr Cys Ser Leu Leu Leu Lys Asp Leu Gln Pro Gln Asp Ser Gly Ser
            100                 105                 110 tat aac ttc cgc ttt gag atc agc gag ggc aac cgc tgg tca gat gtc    384
Tyr Asn Phe Arg Phe Glu Ile Ser Glu Gly Asn Arg Trp Ser Asp Val
        115                 120                 125 aaa ggc aca gtt gtc acc gtg aca gag gtg ccc agc gtg ccc acc att    432
Lys Gly Thr Val Val Thr Val Thr Glu Val Pro Ser Val Pro Thr Ile
    130                 135                 140 gcc ttg cca gcc aag ctg cat gag ggc atg gag gtg gac ttc aac tgc    480
Ala Leu Pro Ala Lys Leu His Glu Gly Met Glu Val Asp Phe Asn Cys
145                 150                 155                 160 tcc act ccc tat gtg tgc ccg acg gag ccg gtc aac cta cag tgg caa    528
Ser Thr Pro Tyr Val Cys Pro Thr Glu Pro Val Asn Leu Gln Trp Gln
                165                 170                 175 ggc cag gat ccc acc cgc tcc gtc acc tcc cac ctc cag aag ctt gag    576
Gly Gln Asp Pro Thr Arg Ser Val Thr Ser His Leu Gln Lys Leu Glu
            180                 185                 190 ccc tcg ggc acc agc cac atg gag acc ctg cac atg gcc ctg tcc tgg    624
```

```
                Pro Ser Gly Thr Ser His Met Glu Thr Leu His Met Ala Leu Ser Trp
                        195                 200                 205 cag gac cat ggc cgg atc ctg agc tgc cag gtc tca gca gcc gaa cgc        672
Gln Asp His Gly Arg Ile Leu Ser Cys Gln Val Ser Ala Ala Glu Arg
        210                 215                 220 agg atg cag aag gag att cac ctc caa gtg cag tat gcc ccc aag ggt        720
Arg Met Gln Lys Glu Ile His Leu Gln Val Gln Tyr Ala Pro Lys Gly
225                 230                 235                 240 gtg gag atc ctt ttc agc cac tcc gga cgg aac gtc ctt cca ggt gat        768
Val Glu Ile Leu Phe Ser His Ser Gly Arg Asn Val Leu Pro Gly Asp
                245                 250                 255 ctg gtc acc ctc agc tgc cag gtg aat agc agc aac cct cag gtc agt        816
Leu Val Thr Leu Ser Cys Gln Val Asn Ser Ser Asn Pro Gln Val Ser
            260                 265                 270 tcc gtg cag tgg gtc aag gat ggg acg aag ctc aaa gac cag aaa cgt        864
Ser Val Gln Trp Val Lys Asp Gly Thr Lys Leu Lys Asp Gln Lys Arg
        275                 280                 285 gta ctt cag ttg cgc cgg gca gcc tgg gct gat gct ggc gtc tac acc        912
Val Leu Gln Leu Arg Arg Ala Ala Trp Ala Asp Ala Gly Val Tyr Thr
    290                 295                 300 tgc caa gcc ggg aat gcc gtg ggc tct tca gtc tca ccc ccg gtc agc        960
Cys Gln Ala Gly Asn Ala Val Gly Ser Ser Val Ser Pro Pro Val Ser
305                 310                 315                 320 ctc cac gtc ttc atg gct gag gtc cag gta agc cct gtg ggc tcc atc       1008
Leu His Val Phe Met Ala Glu Val Gln Val Ser Pro Val Gly Ser Ile
                325                 330                 335 ctg gag aac cag acg gtg acg ctg gcc tgc aat aca cct aag gaa gcg       1056
Leu Glu Asn Gln Thr Val Thr Leu Ala Cys Asn Thr Pro Lys Glu Ala
            340                 345                 350 ccc agc gag ctg cgc tac agc tgg tac aag aac cac gcc ctg ctg gag       1104
Pro Ser Glu Leu Arg Tyr Ser Trp Tyr Lys Asn His Ala Leu Leu Glu
        355                 360                 365 ggc tct cac agc cgc acc ctc cgg ctg cac tca gtc acc agg gcg gat       1152
Gly Ser His Ser Arg Thr Leu Arg Leu His Ser Val Thr Arg Ala Asp
    370                 375                 380 tcg ggc ttc tac ttc tgc gag gtg cag aac gcc cgg ggc aga gag cgc       1200
Ser Gly Phe Tyr Phe Cys Glu Val Gln Asn Ala Arg Gly Arg Glu Arg
385                 390                 395                 400 tct ccc cct gtc agc gtg gtg gtc agc cac cca ccc ctc acc ccg gac       1248
Ser Pro Pro Val Ser Val Val Val Ser His Pro Pro Leu Thr Pro Asp
                405                 410                 415 cta act gcc ttc ctg gag aca cag gcg ggg ctg gtg ggc atc ctc caa       1296
Leu Thr Ala Phe Leu Glu Thr Gln Ala Gly Leu Val Gly Ile Leu Gln
            420                 425                 430 tgc tct gtg gtc agc gag ccc cca gct act ctg gtg ttg tca cac ggg       1344
Cys Ser Val Val Ser Glu Pro Pro Ala Thr Leu Val Leu Ser His Gly
        435                 440                 445 ggc ctc atc ttg gcc tct acc tcc ggg gag ggt gac cac agc cca cgc       1392
Gly Leu Ile Leu Ala Ser Thr Ser Gly Glu Gly Asp His Ser Pro Arg
    450                 455                 460 ttc agt gtc gcc tct gcc ccc aac tcc ctg cgc ctg gag att caa gac       1440
Phe Ser Val Ala Ser Ala Pro Asn Ser Leu Arg Leu Glu Ile Gln Asp
465                 470                 475                 480 ctg ggg cca aca gac agt ggg gaa tac atg tgc tca gcc agc agt tct       1488
Leu Gly Pro Thr Asp Ser Gly Glu Tyr Met Cys Ser Ala Ser Ser Ser
                485                 490                 495 ctt ggg aat gcg tcc tcc acc ctg gac ttc cat gcc aat gca gcc cgc       1536
Leu Gly Asn Ala Ser Ser Thr Leu Asp Phe His Ala Asn Ala Ala Arg
            500                 505                 510 ctc ctc atc agc cca gca gca gag gtg gtg gaa ggg cag gcg gtg aca       1584
```

```
Leu Leu Ile Ser Pro Ala Ala Glu Val Val Glu Gly Gln Ala Val Thr
            515                 520                 525 ctg agc tgc agg agc agc ctg agc ctg atg cct gac acc cgt ttt tcc    1632
Leu Ser Cys Arg Ser Ser Leu Ser Leu Met Pro Asp Thr Arg Phe Ser
530                 535                 540 tgg tac cgg aac ggg gcc ctg ctt ctc gag ggg ccc agc agc agc ctc    1680
Trp Tyr Arg Asn Gly Ala Leu Leu Leu Glu Gly Pro Ser Ser Ser Leu
545                 550                 555                 560 ctg ctc cca gca gcc tcc agc aca gat gcc ggc tca tac cac tgc cgg    1728
Leu Leu Pro Ala Ala Ser Ser Thr Asp Ala Gly Ser Tyr His Cys Arg
                565                 570                 575 gcc cag agc agc cac agc gcc agt ggg ccc tcc tca cct gct gtt ctc    1776
Ala Gln Ser Ser His Ser Ala Ser Gly Pro Ser Ser Pro Ala Val Leu
            580                 585                 590 acc gtg ctc tac gcc cca cgc cag ccc gtg ttc act gcc cag ctg gac    1824
Thr Val Leu Tyr Ala Pro Arg Gln Pro Val Phe Thr Ala Gln Leu Asp
        595                 600                 605 cct gat act gca gga gct ggg gcc gga cgc caa ggc ctc ctc ttg tgc    1872
Pro Asp Thr Ala Gly Ala Gly Ala Gly Arg Gln Gly Leu Leu Leu Cys
610                 615                 620 cgt gtg gac agc gac ccc cca gcc cag ctg cag ctg ctc cac agg ggc    1920
Arg Val Asp Ser Asp Pro Pro Ala Gln Leu Gln Leu Leu His Arg Gly
625                 630                 635                 640 cgt gtt gtg gcc tct tct ctg tca tgg ggg ggc ggc tgc tgc acc tgc    1968
Arg Val Val Ala Ser Ser Leu Ser Trp Gly Gly Gly Cys Cys Thr Cys
                645                 650                 655 gga ggc tgt ttc cac cgc atg aag gtc acc aaa gca ccc aac cta ctg    2016
Gly Gly Cys Phe His Arg Met Lys Val Thr Lys Ala Pro Asn Leu Leu
            660                 665                 670 cgt gta gag atc cga gac ccg gtg ctg gag gac gag ggt gta tac ctg    2064
Arg Val Glu Ile Arg Asp Pro Val Leu Glu Asp Glu Gly Val Tyr Leu
        675                 680                 685 tgc gag gcc agc agc gcc ctg ggc aac gcc tcc gcc tct gca acc ttg    2112
Cys Glu Ala Ser Ser Ala Leu Gly Asn Ala Ser Ala Ser Ala Thr Leu
690                 695                 700 gat gcc cag gcc act gtc ctg gtc atc aca ccg tca cac acg ctg cag    2160
Asp Ala Gln Ala Thr Val Leu Val Ile Thr Pro Ser His Thr Leu Gln
705                 710                 715                 720 gaa ggc att gaa gcc aac ctg act tgc aac gtg agc cgt gaa gcc agc    2208
Glu Gly Ile Glu Ala Asn Leu Thr Cys Asn Val Ser Arg Glu Ala Ser
                725                 730                 735 ggc cct gcc aac ttc tcc tgg ttc cga gat ggg gcg cta tgg gcc cag    2256
Gly Pro Ala Asn Phe Ser Trp Phe Arg Asp Gly Ala Leu Trp Ala Gln
            740                 745                 750 ggc cct ctg gac acc gtg acg ctg cta cct gtg gcc aga act gat gct    2304
Gly Pro Leu Asp Thr Val Thr Leu Leu Pro Val Ala Arg Thr Asp Ala
        755                 760                 765 gcc ctc tat gct tgc cgc atc gtc acc gag gct ggt gct ggc ctc tcc    2352
Ala Leu Tyr Ala Cys Arg Ile Val Thr Glu Ala Gly Ala Gly Leu Ser
770                 775                 780 acc cct gtg gcc ctg aat gtg ctc tat ccc ccc gat cct cca aag ttg    2400
Thr Pro Val Ala Leu Asn Val Leu Tyr Pro Pro Asp Pro Pro Lys Leu
785                 790                 795                 800 tca gcc ctc ctg gac gtg gac cag ggc cac acg gct gtg ttc gtc tgt    2448
Ser Ala Leu Leu Asp Val Asp Gln Gly His Thr Ala Val Phe Val Cys
                805                 810                 815 act gtg gac agt cgc cct ctt gcc cag ttg gcc ctg ttc cgt ggg gaa    2496
Thr Val Asp Ser Arg Pro Leu Ala Gln Leu Ala Leu Phe Arg Gly Glu
            820                 825                 830 cac ctc ctg gcc gcc agc ttg gca ctc cgg ctc ccc cct cat ggc cgc    2544
```

```
                      -continued

His Leu Leu Ala Ala Ser Leu Ala Leu Arg Leu Pro Pro His Gly Arg
        835                 840                 845 ctc cag gcc aaa gcc tcg gcc aac tcc ttg cag cta gag gtc cga gac     2592
Leu Gln Ala Lys Ala Ser Ala Asn Ser Leu Gln Leu Glu Val Arg Asp
850                 855                 860 ttg agc ctt ggg gac tct ggc agc tac cgc tgt gag gcc acc aac atc     2640
Leu Ser Leu Gly Asp Ser Gly Ser Tyr Arg Cys Glu Ala Thr Asn Ile
865                 870                 875                 880 ctt gga tca gcc aac act tct ctt acc ttc cag gtc cga gga gcc tgg     2688
Leu Gly Ser Ala Asn Thr Ser Leu Thr Phe Gln Val Arg Gly Ala Trp
        885                 890                 895 gtc cgg gtg tca ccg tcg cct gag ctc cag gag ggc cag gct gtg gtc     2736
Val Arg Val Ser Pro Ser Pro Glu Leu Gln Glu Gly Gln Ala Val Val
        900                 905                 910 ctg agc tgc cag gta ccc ata ggg gtc ctg gag ggg acc tca tat cgt     2784
Leu Ser Cys Gln Val Pro Ile Gly Val Leu Glu Gly Thr Ser Tyr Arg
        915                 920                 925 tgg tat cgg gat ggc cag ccc ctc cag gag tcc act tcg gcc acg ctc     2832
Trp Tyr Arg Asp Gly Gln Pro Leu Gln Glu Ser Thr Ser Ala Thr Leu
        930                 935                 940 cgt ttt gca gcc ata act ctg agc cag gct gga gcc tac cat tgc caa     2880
Arg Phe Ala Ala Ile Thr Leu Ser Gln Ala Gly Ala Tyr His Cys Gln
945                 950                 955                 960 gcc caa gct cca ggc tca gcc acc acg gac ctg gct gcc cct gtc agc     2928
Ala Gln Ala Pro Gly Ser Ala Thr Thr Asp Leu Ala Ala Pro Val Ser
                965                 970                 975 ctc cac gtg acc tac gca cct cgc cag gcc aca ctc acc acc ctg atg     2976
Leu His Val Thr Tyr Ala Pro Arg Gln Ala Thr Leu Thr Thr Leu Met
                980                 985                 990 gac tca ggc ctc ggg cga ctg ggc ctc ctt ctg tgc cgt gtg aac agt     3024
Asp Ser Gly Leu Gly Arg Leu Gly Leu Leu Leu Cys Arg Val Asn Ser
                995                 1000                1005 gac cct cct gcc cag ctc cga ctg ctc cat ggg agc cgc ctc gtg gcc     3072
Asp Pro Pro Ala Gln Leu Arg Leu Leu His Gly Ser Arg Leu Val Ala
        1010                1015                1020 tct act cta caa ggt gtg gag gag ctt gca ggc agc tct ccc cgc cta     3120
Ser Thr Leu Gln Gly Val Glu Glu Leu Ala Gly Ser Ser Pro Arg Leu
1025                1030                1035                1040 cag gtg gcc aca gcc ccc aac acg ctg cgc ctg gag atc cac aac gca     3168
Gln Val Ala Thr Ala Pro Asn Thr Leu Arg Leu Glu Ile His Asn Ala
                1045                1050                1055 gtg ctg gag gat gaa ggc gtc tac acc tgc gag gcc acc aac acc ctg     3216
Val Leu Glu Asp Glu Gly Val Tyr Thr Cys Glu Ala Thr Asn Thr Leu
                1060                1065                1070 ggt cag acc ttg gcc tcc gcc gcc ttc gat gcc cag gct atg aga gtg     3264
Gly Gln Thr Leu Ala Ser Ala Ala Phe Asp Ala Gln Ala Met Arg Val
                1075                1080                1085 cag gtg tgg ccc aat gcc acc gtg caa gag ggg cag ctg gtg aac ctg     3312
Gln Val Trp Pro Asn Ala Thr Val Gln Glu Gly Gln Leu Val Asn Leu
        1090                1095                1100 acc tgc ctt gta tgg acc acg cac ctg gcc cag ctc acc tac acg tgg     3360
Thr Cys Leu Val Trp Thr Thr His Leu Ala Gln Leu Thr Tyr Thr Trp
1105                1110                1115                1120 tac cga gac cag cag cag ctc cca ggt gct gcc cac tcc atc ctc ctg     3408
Tyr Arg Asp Gln Gln Gln Leu Pro Gly Ala Ala His Ser Ile Leu Leu
                1125                1130                1135 ccc aat gtc act gtc aca gat gcc gcc tcc tac cgc tgt ggc ata ttg     3456
Pro Asn Val Thr Val Thr Asp Ala Ala Ser Tyr Arg Cys Gly Ile Leu
                1140                1145                1150 atc cct ggc cag gca ctc cgc ctc tcc aga cct gtc gcc ctg gat gtc     3504
```

-continued

```
Ile Pro Gly Gln Ala Leu Arg Leu Ser Arg Pro Val Ala Leu Asp Val
        1155                1160                1165 ctc tac gca ccc cgc aga ctg cgc ctg acc cat ctc ttg gag agc cgt      3552
Leu Tyr Ala Pro Arg Arg Leu Arg Leu Thr His Leu Leu Glu Ser Arg
    1170                1175                1180 ggt ggg cag ctg gcc gtg gtg ctg tgc act gtg gac agt cgc cca gct      3600
Gly Gly Gln Leu Ala Val Val Leu Cys Thr Val Asp Ser Arg Pro Ala
1185                1190                1195                1200 gcc cag ctg acc ctc agc cat gct ggc cgc ctc ctg gcc tcc tca acc      3648
Ala Gln Leu Thr Leu Ser His Ala Gly Arg Leu Leu Ala Ser Ser Thr
        1205                1210                1215 gca gcc tct gtc ccc aac acc ctg cgc ctg gag ctg tgg gag ccc cgg      3696
Ala Ala Ser Val Pro Asn Thr Leu Arg Leu Glu Leu Trp Glu Pro Arg
        1220                1225                1230 ccc agt gat gag ggt ctc tac agc tgc tcg gcc cgc agt cct ctg ggc      3744
Pro Ser Asp Glu Gly Leu Tyr Ser Cys Ser Ala Arg Ser Pro Leu Gly
        1235                1240                1245 cag gcc aac aca tcc ctg gag ctg cgg cta gag ggc gtg cag gtg gca      3792
Gln Ala Asn Thr Ser Leu Glu Leu Arg Leu Glu Gly Val Gln Val Ala
        1250                1255                1260 ctg gct cca tcg gcc act gtg ccg gag ggg acc cct gtc aca gtg acc      3840
Leu Ala Pro Ser Ala Thr Val Pro Glu Gly Thr Pro Val Thr Val Thr
1265                1270                1275                1280 tgt gaa gac cct gct gcc cgc cca ccc act ctc tat gtc tgg tac cac      3888
Cys Glu Asp Pro Ala Ala Arg Pro Pro Thr Leu Tyr Val Trp Tyr His
        1285                1290                1295 aac agc cgt tgg ctg cag gag ggg tcg gct gcc tcc ctc tcg ttt cca      3936
Asn Ser Arg Trp Leu Gln Glu Gly Ser Ala Ala Ser Leu Ser Phe Pro
        1300                1305                1310 gcg gct aca cgg gct cac gcg ggc gcc tat acc tgc cag gtc cag gat      3984
Ala Ala Thr Arg Ala His Ala Gly Ala Tyr Thr Cys Gln Val Gln Asp
        1315                1320                1325 gcc cag ggc aca cgc atc tcc cag ccc gca gca ctg cac atc ctc tat      4032
Ala Gln Gly Thr Arg Ile Ser Gln Pro Ala Ala Leu His Ile Leu Tyr
        1330                1335                1340 gcc cct cgg gat gct gtc ctt tcc tcc ttc tgg gac tca agg gcc agc      4080
Ala Pro Arg Asp Ala Val Leu Ser Ser Phe Trp Asp Ser Arg Ala Ser
1345                1350                1355                1360 cct atg gcc gtg gta cag tgc act gtg gac agc gag cca cct gcc gag      4128
Pro Met Ala Val Val Gln Cys Thr Val Asp Ser Glu Pro Pro Ala Glu
        1365                1370                1375 atg acc ctg tcc cgt gat ggc aag gtg ctg gcc acc agc cat ggg gcc      4176
Met Thr Leu Ser Arg Asp Gly Lys Val Leu Ala Thr Ser His Gly Ala
        1380                1385                1390 cac ggc tta gca gtg ggg aca ggc cat gtc cag gtg gcc cgc aac gcc      4224
His Gly Leu Ala Val Gly Thr Gly His Val Gln Val Ala Arg Asn Ala
        1395                1400                1405 ctg cag ctg cgg gtg cag aat gtg ccc tca cgt gac aag gac acc tac      4272
Leu Gln Leu Arg Val Gln Asn Val Pro Ser Arg Asp Lys Asp Thr Tyr
        1410                1415                1420 atc tgc atg gcc cgc aac tcc ttg ggc tca gtc agc acc atg ggg cag      4320
Ile Cys Met Ala Arg Asn Ser Leu Gly Ser Val Ser Thr Met Gly Gln
1425                1430                1435                1440 ctg cag cca gaa ggt gtg cac gtg gtg gcc gag cca ggg ctg gat gtg      4368
Leu Gln Pro Glu Gly Val His Val Val Ala Glu Pro Gly Leu Asp Val
        1445                1450                1455 ccc gaa ggc aca gcg ctg aac ctg agc tgt cgc ttc cct agt ggc cct      4416
Pro Glu Gly Thr Ala Leu Asn Leu Ser Cys Arg Phe Pro Ser Gly Pro
        1460                1465                1470 ggg cac atg ggc aac tcc acc ttt gct tgg ttc cgg aac ggt cgg cag      4464
```

```
                                                                                    -continued
Gly His Met Gly Asn Ser Thr Phe Ala Trp Phe Arg Asn Gly Arg Gln
        1475                1480                1485 cta cac aca gag tct gtg ccc acc ctt acc ttc acc cat gtg gcc cgc           4512
Leu His Thr Glu Ser Val Pro Thr Leu Thr Phe Thr His Val Ala Arg
    1490                1495                1500 gcc cag gct ggc ttg tac cac tgc cag gct gag ctc ccc gcc ggg gct           4560
Ala Gln Ala Gly Leu Tyr His Cys Gln Ala Glu Leu Pro Ala Gly Ala
1505                1510                1515                1520 gcc acc tct gct cca gtc ttg ctc cgg gtg ctc tac cct ccc aag acg           4608
Ala Thr Ser Ala Pro Val Leu Leu Arg Val Leu Tyr Pro Pro Lys Thr
            1525                1530                1535 ccc acc atg act gtt ttt gtg gag ccc gag ggt ggc atc cag ggc att           4656
Pro Thr Met Thr Val Phe Val Glu Pro Glu Gly Gly Ile Gln Gly Ile
        1540                1545                1550 ctg gac tgc cga gtg gac agt gag ccc cta gcc agc ctg acc ctc cac           4704
Leu Asp Cys Arg Val Asp Ser Glu Pro Leu Ala Ser Leu Thr Leu His
    1555                1560                1565 ctg ggc agt cgg ctg gtg gcc tcc agc cag cct cag gct gcc cct gcc           4752
Leu Gly Ser Arg Leu Val Ala Ser Ser Gln Pro Gln Ala Ala Pro Ala
1570                1575                1580 aag ccg cac atc cgc gtc tca gcc agt ccc aat gcc ttg cga gtg gac           4800
Lys Pro His Ile Arg Val Ser Ala Ser Pro Asn Ala Leu Arg Val Asp
1585                1590                1595                1600 atg gag gag ctg aag ccc agt gac cag ggg gag tat gtg tgc tcg gcc           4848
Met Glu Glu Leu Lys Pro Ser Asp Gln Gly Glu Tyr Val Cys Ser Ala
            1605                1610                1615 tcc aat gcc ctg ggc tct gcc tct gct gcc acc tac ttc gga acc aga           4896
Ser Asn Ala Leu Gly Ser Ala Ser Ala Ala Thr Tyr Phe Gly Thr Arg
        1620                1625                1630 gcc ctg cat cgc ctg cat ctg ttc cag cac ctt ctc tgg ttc ctg ggg           4944
Ala Leu His Arg Leu His Leu Phe Gln His Leu Leu Trp Phe Leu Gly
    1635                1640                1645 ctg ctg gcg agc ctc ctc ttc cta ctg ttg ggc ctg ggg gtc tgg tac           4992
Leu Leu Ala Ser Leu Leu Phe Leu Leu Leu Gly Leu Gly Val Trp Tyr
1650                1655                1660 gcc tgg aga cgg gga aat ttt cac aag ctg aga atg ggt gaa tat tca           5040
Ala Trp Arg Arg Gly Asn Phe His Lys Leu Arg Met Gly Glu Tyr Ser
1665                1670                1675                1680 gta gag atg gta tct cgg aag gaa acc acg cag atg tcc act gac cag           5088
Val Glu Met Val Ser Arg Lys Glu Thr Thr Gln Met Ser Thr Asp Gln
            1685                1690                1695 gaa gaa gtt act gga atc ggt gat gat gcg ggc tct gtg aac cag gcg           5136
Glu Glu Val Thr Gly Ile Gly Asp Asp Ala Gly Ser Val Asn Gln Ala
        1700                1705                1710 gca ttt gat cct gcc cac ctc tgt gaa aac aca cag tct gtg aaa agc           5184
Ala Phe Asp Pro Ala His Leu Cys Glu Asn Thr Gln Ser Val Lys Ser
    1715                1720                1725 aca gtc tga cttttatga cctagcttca aaccccaag                                5222
Thr Val *
    1730

<210> SEQ ID NO 2
<211> LENGTH: 1730
<212> TYPE: PRT
<213> ORGANISM: Sus scrofa (pig)

<400> SEQUENCE: 2

Met Asp Phe Leu Leu Leu Leu Leu Leu Ala Ser Ser Ala Leu Ala
1               5                   10                  15

Gly Leu Ala Ser Trp Thr Val Ser Ser Pro Glu Thr Val Gln Gly Ile
            20                  25                  30
```

-continued

Lys Gly Ser Cys Leu Ile Ile Pro Cys Thr Phe Gly Phe Pro Ala Asn
            35                  40                  45

Val Glu Val Pro His Gly Ile Thr Ala Ile Trp Tyr Tyr Asp Tyr Ser
 50                  55                  60

Gly Lys Arg Leu Val Val Ser His Ser Arg Asn Pro Lys Val Val Glu
 65                  70                  75                  80

Asn His Phe Gln Gly Arg Ala Leu Leu Gly Gln Val Glu Gln Arg
                85                  90                  95

Thr Cys Ser Leu Leu Leu Lys Asp Leu Gln Pro Gln Asp Ser Gly Ser
                100                 105                 110

Tyr Asn Phe Arg Phe Glu Ile Ser Glu Gly Asn Arg Trp Ser Asp Val
                115                 120                 125

Lys Gly Thr Val Val Thr Val Thr Glu Val Pro Ser Val Pro Thr Ile
            130                 135                 140

Ala Leu Pro Ala Lys Leu His Glu Gly Met Glu Val Asp Phe Asn Cys
145                 150                 155                 160

Ser Thr Pro Tyr Val Cys Pro Thr Glu Pro Val Asn Leu Gln Trp Gln
                165                 170                 175

Gly Gln Asp Pro Thr Arg Ser Val Thr Ser His Leu Gln Lys Leu Glu
                180                 185                 190

Pro Ser Gly Thr Ser His Met Glu Thr Leu His Met Ala Leu Ser Trp
            195                 200                 205

Gln Asp His Gly Arg Ile Leu Ser Cys Gln Val Ser Ala Ala Glu Arg
            210                 215                 220

Arg Met Gln Lys Glu Ile His Leu Gln Val Gln Tyr Ala Pro Lys Gly
225                 230                 235                 240

Val Glu Ile Leu Phe Ser His Ser Gly Arg Asn Val Leu Pro Gly Asp
                245                 250                 255

Leu Val Thr Leu Ser Cys Gln Val Asn Ser Ser Asn Pro Gln Val Ser
                260                 265                 270

Ser Val Gln Trp Val Lys Asp Gly Thr Lys Leu Lys Asp Gln Lys Arg
            275                 280                 285

Val Leu Gln Leu Arg Arg Ala Trp Ala Asp Ala Gly Val Tyr Thr
            290                 295                 300

Cys Gln Ala Gly Asn Ala Val Gly Ser Ser Val Ser Pro Pro Val Ser
305                 310                 315                 320

Leu His Val Phe Met Ala Glu Val Gln Val Ser Pro Val Gly Ser Ile
                325                 330                 335

Leu Glu Asn Gln Thr Val Thr Leu Ala Cys Asn Thr Pro Lys Glu Ala
            340                 345                 350

Pro Ser Glu Leu Arg Tyr Ser Trp Tyr Lys Asn His Ala Leu Leu Glu
            355                 360                 365

Gly Ser His Ser Arg Thr Leu Arg Leu His Ser Val Thr Arg Ala Asp
 370                 375                 380

Ser Gly Phe Tyr Phe Cys Glu Val Gln Asn Ala Arg Gly Arg Glu Arg
385                 390                 395                 400

Ser Pro Pro Val Ser Val Val Ser His Pro Leu Thr Pro Asp
                405                 410                 415

Leu Thr Ala Phe Leu Glu Thr Gln Ala Gly Leu Val Gly Ile Leu Gln
                420                 425                 430

Cys Ser Val Val Ser Glu Pro Pro Ala Thr Leu Val Leu Ser His Gly
            435                 440                 445

Gly Leu Ile Leu Ala Ser Thr Ser Gly Glu Gly Asp His Ser Pro Arg

```
                450            455             460
     Phe Ser Val Ala Ser Ala Pro Asn Ser Leu Arg Leu Glu Ile Gln Asp
     465                 470                 475                 480

Leu Gly Pro Thr Asp Ser Gly Glu Tyr Met Cys Ser Ala Ser Ser Ser
                     485                 490                 495

Leu Gly Asn Ala Ser Ser Thr Leu Asp Phe His Ala Asn Ala Ala Arg
                 500                 505                 510

Leu Leu Ile Ser Pro Ala Glu Val Val Gly Gln Ala Val Thr
             515                 520                 525

Leu Ser Cys Arg Ser Ser Leu Ser Leu Met Pro Asp Thr Arg Phe Ser
             530                 535                 540

Trp Tyr Arg Asn Gly Ala Leu Leu Glu Gly Pro Ser Ser Ser Leu
     545                 550                 555                 560

Leu Leu Pro Ala Ala Ser Ser Thr Asp Ala Gly Ser Tyr His Cys Arg
                     565                 570                 575

Ala Gln Ser Ser His Ser Ala Ser Gly Pro Ser Ser Pro Ala Val Leu
                 580                 585                 590

Thr Val Leu Tyr Ala Pro Arg Gln Pro Val Phe Thr Ala Gln Leu Asp
                 595                 600                 605

Pro Asp Thr Ala Gly Ala Gly Ala Arg Gln Gly Leu Leu Leu Cys
             610                 615                 620

Arg Val Asp Ser Asp Pro Pro Ala Gln Leu Gln Leu Leu His Arg Gly
     625                 630                 635                 640

Arg Val Val Ala Ser Ser Leu Ser Trp Gly Gly Gly Cys Cys Thr Cys
                     645                 650                 655

Gly Gly Cys Phe His Arg Met Lys Val Thr Lys Ala Pro Asn Leu Leu
                 660                 665                 670

Arg Val Glu Ile Arg Asp Pro Val Leu Glu Asp Glu Gly Val Tyr Leu
                 675                 680                 685

Cys Glu Ala Ser Ser Ala Leu Gly Asn Ala Ser Ala Ser Ala Thr Leu
     690                 695                 700

Asp Ala Gln Ala Thr Val Leu Val Ile Thr Pro Ser His Thr Leu Gln
     705                 710                 715                 720

Glu Gly Ile Glu Ala Asn Leu Thr Cys Asn Val Ser Arg Glu Ala Ser
                     725                 730                 735

Gly Pro Ala Asn Phe Ser Trp Phe Arg Asp Gly Ala Leu Trp Ala Gln
                 740                 745                 750

Gly Pro Leu Asp Thr Val Thr Leu Leu Pro Val Ala Arg Thr Asp Ala
                 755                 760                 765

Ala Leu Tyr Ala Cys Arg Ile Val Thr Glu Ala Gly Ala Gly Leu Ser
     770                 775                 780

Thr Pro Val Ala Leu Asn Val Leu Tyr Pro Pro Asp Pro Pro Lys Leu
     785                 790                 795                 800

Ser Ala Leu Leu Asp Val Asp Gln Gly His Thr Ala Val Phe Val Cys
                     805                 810                 815

Thr Val Asp Ser Arg Pro Leu Ala Gln Leu Ala Leu Phe Arg Gly Glu
                 820                 825                 830

His Leu Leu Ala Ala Ser Leu Ala Leu Arg Leu Pro Pro His Gly Arg
                 835                 840                 845

Leu Gln Ala Lys Ala Ser Ala Asn Ser Leu Gln Leu Glu Val Arg Asp
                 850                 855                 860

Leu Ser Leu Gly Asp Ser Gly Ser Tyr Arg Cys Glu Ala Thr Asn Ile
     865                 870                 875                 880
```

```
Leu Gly Ser Ala Asn Thr Ser Leu Thr Phe Gln Val Arg Gly Ala Trp
                885                 890                 895

Val Arg Val Ser Pro Ser Pro Glu Leu Gln Glu Gly Gln Ala Val Val
            900                 905                 910

Leu Ser Cys Gln Val Pro Ile Gly Val Leu Gly Gly Ser Tyr Arg
        915                 920                 925

Trp Tyr Arg Asp Gly Gln Pro Leu Gln Glu Ser Thr Ser Ala Thr Leu
    930                 935                 940

Arg Phe Ala Ala Ile Thr Leu Ser Gln Ala Gly Ala Tyr His Cys Gln
945                 950                 955                 960

Ala Gln Ala Pro Gly Ser Ala Thr Thr Asp Leu Ala Ala Pro Val Ser
                965                 970                 975

Leu His Val Thr Tyr Ala Pro Arg Gln Ala Thr Leu Thr Thr Leu Met
            980                 985                 990

Asp Ser Gly Leu Gly Arg Leu Gly Leu Leu Cys Arg Val Asn Ser
        995                 1000                1005

Asp Pro Pro Ala Gln Leu Arg Leu Leu His Gly Ser Arg Leu Val Ala
    1010                1015                1020

Ser Thr Leu Gln Gly Val Glu Leu Ala Gly Ser Ser Pro Arg Leu
1025                1030                1035                1040

Gln Val Ala Thr Ala Pro Asn Thr Leu Arg Leu Glu Ile His Asn Ala
            1045                1050                1055

Val Leu Glu Asp Glu Gly Val Tyr Thr Cys Glu Ala Thr Asn Thr Leu
            1060                1065                1070

Gly Gln Thr Leu Ala Ser Ala Ala Phe Asp Ala Gln Ala Met Arg Val
        1075                1080                1085

Gln Val Trp Pro Asn Ala Thr Val Gln Glu Gly Gln Leu Val Asn Leu
    1090                1095                1100

Thr Cys Leu Val Trp Thr Thr His Leu Ala Gln Leu Thr Tyr Thr Trp
1105                1110                1115                1120

Tyr Arg Asp Gln Gln Gln Leu Pro Gly Ala Ala His Ser Ile Leu Leu
            1125                1130                1135

Pro Asn Val Thr Val Thr Asp Ala Ala Ser Tyr Arg Cys Gly Ile Leu
        1140                1145                1150

Ile Pro Gly Gln Ala Leu Arg Leu Ser Arg Pro Val Ala Leu Asp Val
    1155                1160                1165

Leu Tyr Ala Pro Arg Arg Leu Arg Leu Thr His Leu Leu Glu Ser Arg
    1170                1175                1180

Gly Gly Gln Leu Ala Val Val Leu Cys Thr Val Asp Ser Arg Pro Ala
1185                1190                1195                1200

Ala Gln Leu Thr Leu Ser His Ala Gly Arg Leu Leu Ala Ser Ser Thr
        1205                1210                1215

Ala Ala Ser Val Pro Asn Thr Leu Arg Leu Glu Leu Trp Glu Pro Arg
        1220                1225                1230

Pro Ser Asp Glu Gly Leu Tyr Ser Cys Ser Ala Arg Ser Pro Leu Gly
    1235                1240                1245

Gln Ala Asn Thr Ser Leu Glu Leu Arg Leu Glu Gly Val Gln Val Ala
    1250                1255                1260

Leu Ala Pro Ser Ala Thr Val Pro Glu Gly Thr Pro Val Thr Val Thr
1265                1270                1275                1280

Cys Glu Asp Pro Ala Ala Arg Pro Pro Thr Leu Tyr Val Trp Tyr His
            1285                1290                1295

Asn Ser Arg Trp Leu Gln Glu Gly Ser Ala Ala Ser Leu Ser Phe Pro
        1300                1305                1310
```

```
Ala Ala Thr Arg Ala His Ala Gly Ala Tyr Thr Cys Gln Val Gln Asp
        1315                1320                1325

Ala Gln Gly Thr Arg Ile Ser Gln Pro Ala Ala Leu His Ile Leu Tyr
    1330                1335                1340

Ala Pro Arg Asp Ala Val Leu Ser Ser Phe Trp Asp Ser Arg Ala Ser
1345                1350                1355                1360

Pro Met Ala Val Val Gln Cys Thr Val Asp Ser Glu Pro Pro Ala Glu
        1365                1370                1375

Met Thr Leu Ser Arg Asp Gly Lys Val Leu Ala Thr Ser His Gly Ala
    1380                1385                1390

His Gly Leu Ala Val Gly Thr Gly His Val Gln Val Ala Arg Asn Ala
        1395                1400                1405

Leu Gln Leu Arg Val Gln Asn Val Pro Ser Arg Asp Lys Asp Thr Tyr
    1410                1415                1420

Ile Cys Met Ala Arg Asn Ser Leu Gly Ser Val Ser Thr Met Gly Gln
1425                1430                1435                1440

Leu Gln Pro Glu Gly Val His Val Val Ala Glu Pro Gly Leu Asp Val
        1445                1450                1455

Pro Glu Gly Thr Ala Leu Asn Leu Ser Cys Arg Phe Pro Ser Gly Pro
    1460                1465                1470

Gly His Met Gly Asn Ser Thr Phe Ala Trp Phe Arg Asn Gly Arg Gln
    1475                1480                1485

Leu His Thr Glu Ser Val Pro Thr Leu Thr Phe Thr His Val Ala Arg
    1490                1495                1500

Ala Gln Ala Gly Leu Tyr His Cys Gln Ala Glu Leu Pro Ala Gly Ala
1505                1510                1515                1520

Ala Thr Ser Ala Pro Val Leu Leu Arg Val Leu Tyr Pro Pro Lys Thr
        1525                1530                1535

Pro Thr Met Thr Val Phe Val Glu Pro Glu Gly Gly Ile Gln Gly Ile
        1540                1545                1550

Leu Asp Cys Arg Val Asp Ser Glu Pro Leu Ala Ser Leu Thr Leu His
        1555                1560                1565

Leu Gly Ser Arg Leu Val Ala Ser Ser Gln Pro Gln Ala Ala Pro Ala
    1570                1575                1580

Lys Pro His Ile Arg Val Ser Ala Ser Pro Asn Ala Leu Arg Val Asp
1585                1590                1595                1600

Met Glu Glu Leu Lys Pro Ser Asp Gln Gly Glu Tyr Val Cys Ser Ala
                1605                1610                1615

Ser Asn Ala Leu Gly Ser Ala Ser Ala Ala Thr Tyr Phe Gly Thr Arg
        1620                1625                1630

Ala Leu His Arg Leu His Leu Phe Gln His Leu Leu Trp Phe Leu Gly
        1635                1640                1645

Leu Leu Ala Ser Leu Leu Phe Leu Leu Leu Gly Leu Gly Val Trp Tyr
    1650                1655                1660

Ala Trp Arg Arg Gly Asn Phe His Lys Leu Arg Met Gly Glu Tyr Ser
1665                1670                1675                1680

Val Glu Met Val Ser Arg Lys Glu Thr Thr Gln Met Ser Thr Asp Gln
            1685                1690                1695

Glu Glu Val Thr Gly Ile Gly Asp Asp Ala Gly Ser Val Asn Gln Ala
            1700                1705                1710

Ala Phe Asp Pro Ala His Leu Cys Glu Asn Thr Gln Ser Val Lys Ser
        1715                1720                1725

Thr Val
```

-continued

1730

<210> SEQ ID NO 3
<211> LENGTH: 5193
<212> TYPE: DNA
<213> ORGANISM: Sus scrofa (pig)
<220> FEATURE:
<221> NAME/KEY: CDS
<222> LOCATION: (1)...(5193)

<400> SEQUENCE: 3

```
atg gac ttc ctg ctc ctg ctc ctc ctc ctg gct tca tct gct cta gca       48
Met Asp Phe Leu Leu Leu Leu Leu Leu Leu Ala Ser Ser Ala Leu Ala
1               5                   10                  15 ggc ctg gcc tcg tgg acg gtt tcc agc ccc gag acc gtg cag ggc atc       96
Gly Leu Ala Ser Trp Thr Val Ser Ser Pro Glu Thr Val Gln Gly Ile
            20                  25                  30 aag ggc tcc tgc ctc atc atc ccc tgc acc ttc ggc ttc ccg gcc aac      144
Lys Gly Ser Cys Leu Ile Ile Pro Cys Thr Phe Gly Phe Pro Ala Asn
        35                  40                  45 gtg gag gtg ccc cat ggc atc aca gcc atc tgg tac tat gac tac tca      192
Val Glu Val Pro His Gly Ile Thr Ala Ile Trp Tyr Tyr Asp Tyr Ser
    50                  55                  60 ggc aag cgc ctg gta gtg agc cac tcc agg aac cca aag gtg gtg gag      240
Gly Lys Arg Leu Val Val Ser His Ser Arg Asn Pro Lys Val Val Glu
65                  70                  75                  80 aac cac ttc caa ggc cgg gcc ctg ctg ttg ggg cag gtt gaa cag agg      288
Asn His Phe Gln Gly Arg Ala Leu Leu Leu Gly Gln Val Glu Gln Arg
                85                  90                  95 acg tgc agc ctg ctg ctg aag gac ctg cag ccc cag gac tcg ggc tcc      336
Thr Cys Ser Leu Leu Leu Lys Asp Leu Gln Pro Gln Asp Ser Gly Ser
            100                 105                 110 tat aac ttc cgc ttt gag atc agc gag ggc aac cgc tgg tca gat gtc      384
Tyr Asn Phe Arg Phe Glu Ile Ser Glu Gly Asn Arg Trp Ser Asp Val
        115                 120                 125 aaa ggc aca gtt gtc acc gtg aca gag gtg ccc agc gtg ccc acc att      432
Lys Gly Thr Val Val Thr Val Thr Glu Val Pro Ser Val Pro Thr Ile
    130                 135                 140 gcc ttg cca gcc aag ctg cat gag ggc atg gag gtg gac ttc aac tgc      480
Ala Leu Pro Ala Lys Leu His Glu Gly Met Glu Val Asp Phe Asn Cys
145                 150                 155                 160 tcc act ccc tat gtg tgc ccg acg gag ccg gtc aac cta cag tgg caa      528
Ser Thr Pro Tyr Val Cys Pro Thr Glu Pro Val Asn Leu Gln Trp Gln
                165                 170                 175 ggc cag gat ccc acc cgc tcc gtc acc tcc cac ctc cag aag ctt gag      576
Gly Gln Asp Pro Thr Arg Ser Val Thr Ser His Leu Gln Lys Leu Glu
            180                 185                 190 ccc tcg ggc acc agc cac atg gag acc ctg cac atg gcc ctg tcc tgg      624
Pro Ser Gly Thr Ser His Met Glu Thr Leu His Met Ala Leu Ser Trp
        195                 200                 205 cag gac cat ggc cgg atc ctg agc tgc cag gtc tca gca gcc gaa cgc      672
Gln Asp His Gly Arg Ile Leu Ser Cys Gln Val Ser Ala Ala Glu Arg
    210                 215                 220 agg atg cag aag gag att cac ctc caa gtg cag tat gcc ccc aag ggt      720
Arg Met Gln Lys Glu Ile His Leu Gln Val Gln Tyr Ala Pro Lys Gly
225                 230                 235                 240 gtg gag atc ctt ttc agc cac tcc gga cgg aac gtc ctt cca ggt gat      768
Val Glu Ile Leu Phe Ser His Ser Gly Arg Asn Val Leu Pro Gly Asp
                245                 250                 255 ctg gtc acc ctc agc tgc cag gtg aat agc agc aac cct cag gtc agt      816
Leu Val Thr Leu Ser Cys Gln Val Asn Ser Ser Asn Pro Gln Val Ser
            260                 265                 270
```

|   |   |   |   |   |   |   |   |   |   |   |   |   |   |   |   |   |
|---|---|---|---|---|---|---|---|---|---|---|---|---|---|---|---|---|
| tcc | gtg | cag | tgg | gtc | aag | gat | ggg | acg | aag | ctc | aaa | gac | cag | aaa | cgt | 864 |
| Ser | Val | Gln | Trp | Val | Lys | Asp | Gly | Thr | Lys | Leu | Lys | Asp | Gln | Lys | Arg |   |
|   |   | 275 |   |   |   | 280 |   |   |   | 285 |   |   |   |   |   |   |

|   |   |   |   |   |   |   |   |   |   |   |   |   |   |   |   |   |
|---|---|---|---|---|---|---|---|---|---|---|---|---|---|---|---|---|
| gta | ctg | cag | ttg | cgc | cgg | gca | gcc | tgg | gct | gat | gct | ggc | gtc | tac | acc | 912 |
| Val | Leu | Gln | Leu | Arg | Arg | Ala | Ala | Trp | Ala | Asp | Ala | Gly | Val | Tyr | Thr |   |
| 290 |   |   |   |   | 295 |   |   |   |   | 300 |   |   |   |   |   |   |

|   |   |   |   |   |   |   |   |   |   |   |   |   |   |   |   |   |
|---|---|---|---|---|---|---|---|---|---|---|---|---|---|---|---|---|
| tgc | caa | gcc | ggg | aat | gcc | gtg | ggc | tct | tca | gtc | tca | ccc | ccg | gtc | agc | 960 |
| Cys | Gln | Ala | Gly | Asn | Ala | Val | Gly | Ser | Ser | Val | Ser | Pro | Pro | Val | Ser |   |
| 305 |   |   |   | 310 |   |   |   |   | 315 |   |   |   |   | 320 |   |   |

|   |   |   |   |   |   |   |   |   |   |   |   |   |   |   |   |   |
|---|---|---|---|---|---|---|---|---|---|---|---|---|---|---|---|---|
| ctc | cac | gtc | ttc | atg | gct | gag | gtc | cag | gta | agc | cct | gtg | ggc | tcc | atc | 1008 |
| Leu | His | Val | Phe | Met | Ala | Glu | Val | Gln | Val | Ser | Pro | Val | Gly | Ser | Ile |   |
|   |   |   |   | 325 |   |   |   |   | 330 |   |   |   |   | 335 |   |   |

|   |   |   |   |   |   |   |   |   |   |   |   |   |   |   |   |   |
|---|---|---|---|---|---|---|---|---|---|---|---|---|---|---|---|---|
| ctg | gag | aac | cag | acg | gtg | acg | ctg | gcc | tgc | aat | aca | cct | aag | gaa | gcg | 1056 |
| Leu | Glu | Asn | Gln | Thr | Val | Thr | Leu | Ala | Cys | Asn | Thr | Pro | Lys | Glu | Ala |   |
|   |   |   | 340 |   |   |   |   | 345 |   |   |   |   | 350 |   |   |   |

|   |   |   |   |   |   |   |   |   |   |   |   |   |   |   |   |   |
|---|---|---|---|---|---|---|---|---|---|---|---|---|---|---|---|---|
| ccc | agc | gag | ctg | cgc | tac | agc | tgg | tac | aag | aac | cac | gcc | ctg | ctg | gag | 1104 |
| Pro | Ser | Glu | Leu | Arg | Tyr | Ser | Trp | Tyr | Lys | Asn | His | Ala | Leu | Leu | Glu |   |
|   |   | 355 |   |   |   |   | 360 |   |   |   |   | 365 |   |   |   |   |

|   |   |   |   |   |   |   |   |   |   |   |   |   |   |   |   |   |
|---|---|---|---|---|---|---|---|---|---|---|---|---|---|---|---|---|
| ggc | tct | cac | agc | cgc | acc | ctc | cgg | ctg | cac | tca | gtt | acc | agg | gcg | gat | 1152 |
| Gly | Ser | His | Ser | Arg | Thr | Leu | Arg | Leu | His | Ser | Val | Thr | Arg | Ala | Asp |   |
|   | 370 |   |   |   |   | 375 |   |   |   |   | 380 |   |   |   |   |   |

|   |   |   |   |   |   |   |   |   |   |   |   |   |   |   |   |   |
|---|---|---|---|---|---|---|---|---|---|---|---|---|---|---|---|---|
| tcg | ggc | ttc | tac | ttc | tgc | gag | gtg | cag | aac | gcc | cgg | ggc | aga | gag | cgc | 1200 |
| Ser | Gly | Phe | Tyr | Phe | Cys | Glu | Val | Gln | Asn | Ala | Arg | Gly | Arg | Glu | Arg |   |
| 385 |   |   |   |   | 390 |   |   |   |   | 395 |   |   |   |   | 400 |   |

|   |   |   |   |   |   |   |   |   |   |   |   |   |   |   |   |   |
|---|---|---|---|---|---|---|---|---|---|---|---|---|---|---|---|---|
| tct | ccc | cct | gtc | agc | gtg | gtg | gtc | agc | cac | cca | ccc | ctc | acc | ccg | gac | 1248 |
| Ser | Pro | Pro | Val | Ser | Val | Val | Val | Ser | His | Pro | Pro | Leu | Thr | Pro | Asp |   |
|   |   |   |   | 405 |   |   |   |   | 410 |   |   |   |   | 415 |   |   |

|   |   |   |   |   |   |   |   |   |   |   |   |   |   |   |   |   |
|---|---|---|---|---|---|---|---|---|---|---|---|---|---|---|---|---|
| cta | act | gcc | ttc | ctg | gag | aca | cag | gcg | ggg | ctg | gtg | ggc | atc | ctc | caa | 1296 |
| Leu | Thr | Ala | Phe | Leu | Glu | Thr | Gln | Ala | Gly | Leu | Val | Gly | Ile | Leu | Gln |   |
|   |   |   | 420 |   |   |   |   | 425 |   |   |   |   | 430 |   |   |   |

|   |   |   |   |   |   |   |   |   |   |   |   |   |   |   |   |   |
|---|---|---|---|---|---|---|---|---|---|---|---|---|---|---|---|---|
| tgc | tct | gtg | gtc | agc | gag | ccc | cca | gct | act | ctg | gtg | ttg | tca | cac | ggg | 1344 |
| Cys | Ser | Val | Val | Ser | Glu | Pro | Pro | Ala | Thr | Leu | Val | Leu | Ser | His | Gly |   |
|   |   | 435 |   |   |   |   | 440 |   |   |   |   | 445 |   |   |   |   |

|   |   |   |   |   |   |   |   |   |   |   |   |   |   |   |   |   |
|---|---|---|---|---|---|---|---|---|---|---|---|---|---|---|---|---|
| ggc | ctc | atc | ttg | gcc | tct | acc | tcc | ggg | gag | ggt | gac | cac | agc | cca | cgc | 1392 |
| Gly | Leu | Ile | Leu | Ala | Ser | Thr | Ser | Gly | Glu | Gly | Asp | His | Ser | Pro | Arg |   |
| 450 |   |   |   |   | 455 |   |   |   |   | 460 |   |   |   |   |   |   |

|   |   |   |   |   |   |   |   |   |   |   |   |   |   |   |   |   |
|---|---|---|---|---|---|---|---|---|---|---|---|---|---|---|---|---|
| ttc | agt | gtc | gcc | tct | gcc | ccc | aac | tcc | ctg | cgc | ctg | gag | att | caa | gac | 1440 |
| Phe | Ser | Val | Ala | Ser | Ala | Pro | Asn | Ser | Leu | Arg | Leu | Glu | Ile | Gln | Asp |   |
| 465 |   |   |   | 470 |   |   |   |   | 475 |   |   |   |   | 480 |   |   |

|   |   |   |   |   |   |   |   |   |   |   |   |   |   |   |   |   |
|---|---|---|---|---|---|---|---|---|---|---|---|---|---|---|---|---|
| ctg | ggg | cca | aca | gac | agt | ggg | gaa | tac | atg | tgc | tca | gcc | agc | agt | tct | 1488 |
| Leu | Gly | Pro | Thr | Asp | Ser | Gly | Glu | Tyr | Met | Cys | Ser | Ala | Ser | Ser | Ser |   |
|   |   |   |   | 485 |   |   |   |   | 490 |   |   |   |   | 495 |   |   |

|   |   |   |   |   |   |   |   |   |   |   |   |   |   |   |   |   |
|---|---|---|---|---|---|---|---|---|---|---|---|---|---|---|---|---|
| ctt | ggg | aat | gcg | tcc | tcc | acc | ctg | gac | ttc | cat | gcc | aat | gca | gcc | cgc | 1536 |
| Leu | Gly | Asn | Ala | Ser | Ser | Thr | Leu | Asp | Phe | His | Ala | Asn | Ala | Ala | Arg |   |
|   |   |   | 500 |   |   |   |   | 505 |   |   |   |   | 510 |   |   |   |

|   |   |   |   |   |   |   |   |   |   |   |   |   |   |   |   |   |
|---|---|---|---|---|---|---|---|---|---|---|---|---|---|---|---|---|
| ctc | ctc | atc | agc | cca | gca | gca | gag | gtg | gtg | gaa | ggg | cag | gcg | gtg | aca | 1584 |
| Leu | Leu | Ile | Ser | Pro | Ala | Ala | Glu | Val | Val | Glu | Gly | Gln | Ala | Val | Thr |   |
|   |   | 515 |   |   |   |   | 520 |   |   |   |   | 525 |   |   |   |   |

|   |   |   |   |   |   |   |   |   |   |   |   |   |   |   |   |   |
|---|---|---|---|---|---|---|---|---|---|---|---|---|---|---|---|---|
| ctg | agc | tgc | agg | agc | agc | ctg | agc | ctg | atg | cct | gac | acc | cgt | ttt | tcc | 1632 |
| Leu | Ser | Cys | Arg | Ser | Ser | Leu | Ser | Leu | Met | Pro | Asp | Thr | Arg | Phe | Ser |   |
|   | 530 |   |   |   |   | 535 |   |   |   |   | 540 |   |   |   |   |   |

|   |   |   |   |   |   |   |   |   |   |   |   |   |   |   |   |   |
|---|---|---|---|---|---|---|---|---|---|---|---|---|---|---|---|---|
| tgg | tac | ctg | aac | ggg | gcc | ctg | att | ctc | gag | ggg | ccc | agc | agc | agc | ctc | 1680 |
| Trp | Tyr | Leu | Asn | Gly | Ala | Leu | Ile | Leu | Glu | Gly | Pro | Ser | Ser | Ser | Leu |   |
| 545 |   |   |   |   | 550 |   |   |   |   | 555 |   |   |   |   | 560 |   |

|   |   |   |   |   |   |   |   |   |   |   |   |   |   |   |   |   |
|---|---|---|---|---|---|---|---|---|---|---|---|---|---|---|---|---|
| ctg | ctc | cca | gca | gcc | tcc | agc | aca | gat | gcc | ggc | tca | tac | cac | tgc | cgg | 1728 |
| Leu | Leu | Pro | Ala | Ala | Ser | Ser | Thr | Asp | Ala | Gly | Ser | Tyr | His | Cys | Arg |   |
|   |   |   |   | 565 |   |   |   |   | 570 |   |   |   |   | 575 |   |   |

|   |   |   |   |   |   |   |   |   |   |   |   |   |   |   |   |   |
|---|---|---|---|---|---|---|---|---|---|---|---|---|---|---|---|---|
| gcc | cag | aac | agc | cac | agc | acc | agc | ggg | ccc | tcc | tca | cct | gct | gtt | ctc | 1776 |
| Ala | Gln | Asn | Ser | His | Ser | Thr | Ser | Gly | Pro | Ser | Ser | Pro | Ala | Val | Leu |   |
|   |   |   |   | 580 |   |   |   |   | 585 |   |   |   |   | 590 |   |   |

```
acc gtg ctc tac gcc cca cgc cag ccc gtg ttc act gcc cag ctg gac    1824
Thr Val Leu Tyr Ala Pro Arg Gln Pro Val Phe Thr Ala Gln Leu Asp
        595                 600                 605 cct gat act gca gga gct ggg gcc gga cgc caa ggc ctc ctc ttg tgc    1872
Pro Asp Thr Ala Gly Ala Gly Arg Gln Gly Leu Leu Leu Cys
610                 615                 620 cgt gtg gac agc gac ccc cca gcc cag ctg cag ctg ctc cac agg ggc    1920
Arg Val Asp Ser Asp Pro Pro Ala Gln Leu Gln Leu Leu His Arg Gly
625                 630                 635                 640 cgt gtt gtg gcc tct tct ctg tca tgg ggg ggc ggc tgc tgc acc tgc    1968
Arg Val Val Ala Ser Ser Leu Ser Trp Gly Gly Gly Cys Cys Thr Cys
                645                 650                 655 gga ggc tgt ttc cac cgc atg aag gtc acc aaa gca ccc aac cta ctg    2016
Gly Gly Cys Phe His Arg Met Lys Val Thr Lys Ala Pro Asn Leu Leu
            660                 665                 670 cgt gta gag atc cga gac ccg gtg ctg gag gat gag ggt gtg tac ctg    2064
Arg Val Glu Ile Arg Asp Pro Val Leu Glu Asp Glu Gly Val Tyr Leu
        675                 680                 685 tgc gag gcc agc agc gcc ctg ggc aac gcc tcc gcc tct gca acc ttg    2112
Cys Glu Ala Ser Ser Ala Leu Gly Asn Ala Ser Ala Ser Ala Thr Leu
690                 695                 700 gat gcc cag gcc act gtc ctg gtc atc aca ccg tca cac acg ctg cag    2160
Asp Ala Gln Ala Thr Val Leu Val Ile Thr Pro Ser His Thr Leu Gln
705                 710                 715                 720 gaa ggc att gaa gcc aac ctg act tgc aac gtg agc cgt gaa gcc agc    2208
Glu Gly Ile Glu Ala Asn Leu Thr Cys Asn Val Ser Arg Glu Ala Ser
                725                 730                 735 ggc cct gcc aac ttc tcc tgg ttc cga gat ggg gcg cta tgg gcc cag    2256
Gly Pro Ala Asn Phe Ser Trp Phe Arg Asp Gly Ala Leu Trp Ala Gln
            740                 745                 750 ggc cct ctg gac acc gtg acg ctg cta cct gtg gcc aga act gat gct    2304
Gly Pro Leu Asp Thr Val Thr Leu Leu Pro Val Ala Arg Thr Asp Ala
        755                 760                 765 gcc ctc tat gct tgc cgc atc gtc acc gag gct ggt gct ggc ctc tcc    2352
Ala Leu Tyr Ala Cys Arg Ile Val Thr Glu Ala Gly Ala Gly Leu Ser
770                 775                 780 acc cct gtg gcc ctg aat gtg ctc tat ccc ccc gat cct cca aag ttg    2400
Thr Pro Val Ala Leu Asn Val Leu Tyr Pro Pro Asp Pro Pro Lys Leu
785                 790                 795                 800 tca gcc ctc ctg gac gtg gac cag ggc cac acg gct gtg ttc gtc tgt    2448
Ser Ala Leu Leu Asp Val Asp Gln Gly His Thr Ala Val Phe Val Cys
                805                 810                 815 act gtg gac agt cgc cct ctt gcc cag ttg gcc ctg ttc cgt ggg gaa    2496
Thr Val Asp Ser Arg Pro Leu Ala Gln Leu Ala Leu Phe Arg Gly Glu
            820                 825                 830 cac ctc ctg gcc gcc agc tcg gca ctc cgg ctc ccc cct cgt ggc cgc    2544
His Leu Leu Ala Ala Ser Ser Ala Leu Arg Leu Pro Pro Arg Gly Arg
        835                 840                 845 ctc cag gcc aaa gcc tcg gcc aac tcc ttg cag cta gag gtc cga gac    2592
Leu Gln Ala Lys Ala Ser Ala Asn Ser Leu Gln Leu Glu Val Arg Asp
850                 855                 860 ttg agc ctt ggg gac tct ggc agc tac cac tgt gag gcc acc aac atc    2640
Leu Ser Leu Gly Asp Ser Gly Ser Tyr His Cys Glu Ala Thr Asn Ile
865                 870                 875                 880 ctt gga tca gcc aac act tct ctt acc ttc cag gtc cga gga gcc tgg    2688
Leu Gly Ser Ala Asn Thr Ser Leu Thr Phe Gln Val Arg Gly Ala Trp
                885                 890                 895 gtc cgg gtg tca ccg tcg cct gag ctc cag gag ggc cag gct gtg gtc    2736
Val Arg Val Ser Pro Ser Pro Glu Leu Gln Glu Gly Gln Ala Val Val
            900                 905                 910
```

-continued

| | |
|---|---|
| ctg agc tgc cag gta ccc ata ggg gtc ctg gag ggg acc tca tat cgt<br>Leu Ser Cys Gln Val Pro Ile Gly Val Leu Glu Gly Thr Ser Tyr Arg<br>    915                        920                      925 | 2784 |
| tgg tat cgg gat ggc cag ccc ctc cag gag tcc act tcg gcc acg ctc<br>Trp Tyr Arg Asp Gly Gln Pro Leu Gln Glu Ser Thr Ser Ala Thr Leu<br>    930                        935                      940 | 2832 |
| cgt ttt gca gcc ata act ctg agc cag gct gga gcc tac cat tgc caa<br>Arg Phe Ala Ala Ile Thr Leu Ser Gln Ala Gly Ala Tyr His Cys Gln<br>945                        950                      955                    960 | 2880 |
| gcc caa gct cca ggc tca gcc acc acg gac ctg gct gcc cct gtc agc<br>Ala Gln Ala Pro Gly Ser Ala Thr Thr Asp Leu Ala Ala Pro Val Ser<br>                        965                      970                      975 | 2928 |
| ctc cac gtg acc tac gca cct cgc cag gcc aca ctc acc acc ctg atg<br>Leu His Val Thr Tyr Ala Pro Arg Gln Ala Thr Leu Thr Thr Leu Met<br>    980                        985                      990 | 2976 |
| gac tca ggc ctc ggg cga ctg ggc ctc ctt ctg tgc cgt gtg aac agt<br>Asp Ser Gly Leu Gly Arg Leu Gly Leu Leu Leu Cys Arg Val Asn Ser<br>                        995                      1000                1005 | 3024 |
| gac cct cct gcc cag ctc cga ctg ctc cat ggg agc cgc ctc gtg gcc<br>Asp Pro Pro Ala Gln Leu Arg Leu Leu His Gly Ser Arg Leu Val Ala<br>    1010                      1015                    1020 | 3072 |
| tct act cta caa ggt gtg gag gag ctt gca ggc agc tct ccc cgc cta<br>Ser Thr Leu Gln Gly Val Glu Glu Leu Ala Gly Ser Ser Pro Arg Leu<br>1025                   1030                   1035                   1040 | 3120 |
| cag gtg gcc aca gcc ccc aac acg ctg cgc ctg gag atc cac aac gca<br>Gln Val Ala Thr Ala Pro Asn Thr Leu Arg Leu Glu Ile His Asn Ala<br>                        1045                    1050                    1055 | 3168 |
| gtg ctg gag gat gaa ggc gtc tac acc tgc gag gcc acc aac acc ctg<br>Val Leu Glu Asp Glu Gly Val Tyr Thr Cys Glu Ala Thr Asn Thr Leu<br>    1060                      1065                    1070 | 3216 |
| ggt cag acc ttg gcc tcc gcc gcc ttc gat gcc cag gct atg aga gtg<br>Gly Gln Thr Leu Ala Ser Ala Ala Phe Asp Ala Gln Ala Met Arg Val<br>                        1075                    1080                    1085 | 3264 |
| cag gtg tgg ccc aat gcc acc gtg caa gag ggg cag ctg gtg aac ctg<br>Gln Val Trp Pro Asn Ala Thr Val Gln Glu Gly Gln Leu Val Asn Leu<br>    1090                      1095                    1100 | 3312 |
| acc tgc ctt gta tgg acc acg cac ctg gcc cag ctc acc tac acg tgg<br>Thr Cys Leu Val Trp Thr Thr His Leu Ala Gln Leu Thr Tyr Thr Trp<br>1105                   1110                   1115                   1120 | 3360 |
| tac cga gac cag cag cag ctc cca ggt gct gcc cac tcc atc ctc ctg<br>Tyr Arg Asp Gln Gln Gln Leu Pro Gly Ala Ala His Ser Ile Leu Leu<br>                        1125                    1130                    1135 | 3408 |
| ccc aat gtc act gtc aca gat gcc gcc tcc tac cgc tgt ggc ata ttg<br>Pro Asn Val Thr Val Thr Asp Ala Ala Ser Tyr Arg Cys Gly Ile Leu<br>                        1140                    1145                    1150 | 3456 |
| atc cct ggc cag gca ctc cgc ctc tcc aga cct gtc gcc ctg gat gtc<br>Ile Pro Gly Gln Ala Leu Arg Leu Ser Arg Pro Val Ala Leu Asp Val<br>                    1155                    1160                    1165 | 3504 |
| ctc tac gca ccc cgc aga ctg cgc ctg acc cat ctc ttg gag agc cgt<br>Leu Tyr Ala Pro Arg Arg Leu Arg Leu Thr His Leu Leu Glu Ser Arg<br>    1170                      1175                    1180 | 3552 |
| ggt ggg cag ctg gcc gtg gtg ctg tgc act gtg gac agt cgc cca gct<br>Gly Gly Gln Leu Ala Val Val Leu Cys Thr Val Asp Ser Arg Pro Ala<br>1185                   1190                   1195                   1200 | 3600 |
| gcc cag ctg acc ctc agc cat gct ggc cgc ctc ctg gcc tcc tca acc<br>Ala Gln Leu Thr Leu Ser His Ala Gly Arg Leu Leu Ala Ser Ser Thr<br>                        1205                    1210                    1215 | 3648 |
| gca gcc tct gtc ccc aac acc ctg cgc ctg gag ctg tgg gag ccc cgg<br>Ala Ala Ser Val Pro Asn Thr Leu Arg Leu Glu Leu Trp Glu Pro Arg<br>    1220                      1225                    1230 | 3696 |

| | |
|---|---|
| ccc agt gat gag ggt ctc tac agc tgc tcg gcc cgc agt cct ctg ggc<br>Pro Ser Asp Glu Gly Leu Tyr Ser Cys Ser Ala Arg Ser Pro Leu Gly<br>    1235                       1240                   1245 | 3744 |
| cag gcc aac aca tcc ctg gag ctg cgg cta gag ggc gtg cag gtg gca<br>Gln Ala Asn Thr Ser Leu Glu Leu Arg Leu Glu Gly Val Gln Val Ala<br>1250                    1255                 1260 | 3792 |
| ctg gct cca tcg gcc act gtg ccg gag ggg gcc cct gtc aca gtg acc<br>Leu Ala Pro Ser Ala Thr Val Pro Glu Gly Ala Pro Val Thr Val Thr<br>1265                 1270               1275               1280 | 3840 |
| tgt gaa gac cct gct gcc cgc cca ccc act ctc tat gtc tgg tac cac<br>Cys Glu Asp Pro Ala Ala Arg Pro Pro Thr Leu Tyr Val Trp Tyr His<br>                  1285                 1290                1295 | 3888 |
| aac agc cgt tgg ctg cag gag ggg tcg gct gcc tcc ctc tcg ttt cca<br>Asn Ser Arg Trp Leu Gln Glu Gly Ser Ala Ala Ser Leu Ser Phe Pro<br>             1300                  1305               1310 | 3936 |
| gcg gct aca cgg gct cac gcg ggc gcc tat acc tgc cag gtc cag gat<br>Ala Ala Thr Arg Ala His Ala Gly Ala Tyr Thr Cys Gln Val Gln Asp<br>1315                   1320                  1325 | 3984 |
| gcc cag ggc aca cgc atc tcc cag ccc gca gca ctg cac atc ctc tat<br>Ala Gln Gly Thr Arg Ile Ser Gln Pro Ala Ala Leu His Ile Leu Tyr<br>          1330                 1335               1340 | 4032 |
| gcc cct cgg gat gct gtc ctt tcc tcc ttc tgg gac tca agg gcc agc<br>Ala Pro Arg Asp Ala Val Leu Ser Ser Phe Trp Asp Ser Arg Ala Ser<br>1345                   1350                 1355               1360 | 4080 |
| cct atg gcc gtg gta cag tgc act gtg gac agc gag cca cct gcc gag<br>Pro Met Ala Val Val Gln Cys Thr Val Asp Ser Glu Pro Pro Ala Glu<br>                 1365                1370                1375 | 4128 |
| atg acc ctg tcc cat gat ggc aag gtg ctg gcc acc agc cat ggg gtc<br>Met Thr Leu Ser His Asp Gly Lys Val Leu Ala Thr Ser His Gly Val<br>             1380                  1385               1390 | 4176 |
| cac ggc tta gca gtg ggg aca ggc cat gtc cag gtg gcc cgc aac gcc<br>His Gly Leu Ala Val Gly Thr Gly His Val Gln Val Ala Arg Asn Ala<br>          1395                 1400               1405 | 4224 |
| ctg cag ctg cgg gtg cag aat gtg ccc tca cgt gac aag gac acc tac<br>Leu Gln Leu Arg Val Gln Asn Val Pro Ser Arg Asp Lys Asp Thr Tyr<br>1410                   1415                  1420 | 4272 |
| gtc tgc atg gac cgc aac tcc ttg ggc tca gtc agc acc atg ggg cag<br>Val Cys Met Asp Arg Asn Ser Leu Gly Ser Val Ser Thr Met Gly Gln<br>1425                   1430                 1435               1440 | 4320 |
| ctg cag cca gaa ggt gtg cac gtg gta gct gag cca ggg ctg gat gtg<br>Leu Gln Pro Glu Gly Val His Val Val Ala Glu Pro Gly Leu Asp Val<br>                 1445                1450                1455 | 4368 |
| cct gaa ggc aca gcg ctg aac ctg agc tgt cgc ctc cct agt ggc cct<br>Pro Glu Gly Thr Ala Leu Asn Leu Ser Cys Arg Leu Pro Ser Gly Pro<br>             1460                  1465               1470 | 4416 |
| ggg cac ata ggc aac tcc acc ttt gct tgg ttc cgg aac ggt cgg cag<br>Gly His Ile Gly Asn Ser Thr Phe Ala Trp Phe Arg Asn Gly Arg Gln<br>           1475                 1480               1485 | 4464 |
| cta cac aca gag tct gtg ccc acc ctt acc ttc acc cat gtg gcc cgc<br>Leu His Thr Glu Ser Val Pro Thr Leu Thr Phe Thr His Val Ala Arg<br>1490                   1495                  1500 | 4512 |
| gcc caa gct ggc ttg tac cac tgc cag gct gag ctc ccc gcc ggg gct<br>Ala Gln Ala Gly Leu Tyr His Cys Gln Ala Glu Leu Pro Ala Gly Ala<br>1505                   1510                  1515               1520 | 4560 |
| gcc acc tct gct cca gtc ttg ctc cgg gtg ctc tac cct ccc aag acg<br>Ala Thr Ser Ala Pro Val Leu Leu Arg Val Leu Tyr Pro Pro Lys Thr<br>                 1525                1530                1535 | 4608 |
| ccc acc atg act gtt ttt gtg gag ccc gag ggt ggc atc cag ggc att<br>Pro Thr Met Thr Val Phe Val Glu Pro Glu Gly Gly Ile Gln Gly Ile<br>             1540                  1545               1550 | 4656 |

```
ctg gac tgc cga gtg gac agt gag ccc cta gcc agc ctg acc ctc cac       4704
Leu Asp Cys Arg Val Asp Ser Glu Pro Leu Ala Ser Leu Thr Leu His
        1555                1560                1565 ctg ggc agt cgg ctg gtg gcc tcc agc cag cct cag gct gcc cct gcc       4752
Leu Gly Ser Arg Leu Val Ala Ser Ser Gln Pro Gln Ala Ala Pro Ala
    1570                1575                1580 aag ccg cac atc cgc gtc tca gcc agt ccc aat gcc ttg cga gtg gac       4800
Lys Pro His Ile Arg Val Ser Ala Ser Pro Asn Ala Leu Arg Val Asp
1585                1590                1595                1600 atg gag gag ctg aag ccc agt gac cag ggg gag tat gtg tgc tcg gcc       4848
Met Glu Glu Leu Lys Pro Ser Asp Gln Gly Glu Tyr Val Cys Ser Ala
                1605                1610                1615 tcc aat gcc ctg ggc tct gcc tct gct gcc acc tac ttc gga acc aga       4896
Ser Asn Ala Leu Gly Ser Ala Ser Ala Ala Thr Tyr Phe Gly Thr Arg
        1620                1625                1630 gcc ctg cat cgc ctg cat ctg ttc cag cac ctt ctc tgg ttc ctg ggg       4944
Ala Leu His Arg Leu His Leu Phe Gln His Leu Leu Trp Phe Leu Gly
    1635                1640                1645 ctg ctg gcg agc ctc ctc ttc cta ctg ttg ggc ctg ggg gtc tgg tac       4992
Leu Leu Ala Ser Leu Leu Phe Leu Leu Leu Gly Leu Gly Val Trp Tyr
1650                1655                1660 gcc tgg aga cgg gga aat ttt tac aag ctg aga atg ggc gaa tat tca       5040
Ala Trp Arg Arg Gly Asn Phe Tyr Lys Leu Arg Met Gly Glu Tyr Ser
1665                1670                1675                1680 gta gag atg gta tct cgg aag gaa acc acg cag atg tcc act gac cag       5088
Val Glu Met Val Ser Arg Lys Glu Thr Thr Gln Met Ser Thr Asp Gln
                1685                1690                1695 gaa gaa gtt act gga atc ggt gat gat gcg ggc tct gtg aac cag gcg       5136
Glu Glu Val Thr Gly Ile Gly Asp Asp Ala Gly Ser Val Asn Gln Ala
        1700                1705                1710 gca ttt gat cct gcc cac ctc tgt gaa aac aca cag tct gtg aaa agc       5184
Ala Phe Asp Pro Ala His Leu Cys Glu Asn Thr Gln Ser Val Lys Ser
    1715                1720                1725 aca gtc tga                                                           5193
Thr Val  *
    1730

<210> SEQ ID NO 4
<211> LENGTH: 1730
<212> TYPE: PRT
<213> ORGANISM: Sus scrofa (pig)

<400> SEQUENCE: 4

Met Asp Phe Leu Leu Leu Leu Leu Leu Ala Ser Ser Ala Leu Ala
  1               5                  10                  15

Gly Leu Ala Ser Trp Thr Val Ser Ser Pro Glu Thr Val Gln Gly Ile
             20                  25                  30

Lys Gly Ser Cys Leu Ile Ile Pro Cys Thr Phe Gly Phe Pro Ala Asn
         35                  40                  45

Val Glu Val Pro His Gly Ile Thr Ala Ile Trp Tyr Tyr Asp Tyr Ser
     50                  55                  60

Gly Lys Arg Leu Val Val Ser His Ser Arg Asn Pro Lys Val Val Glu
 65                  70                  75                  80

Asn His Phe Gln Gly Arg Ala Leu Leu Leu Gly Gln Val Glu Gln Arg
                 85                  90                  95

Thr Cys Ser Leu Leu Leu Lys Asp Leu Gln Pro Gln Asp Ser Gly Ser
            100                 105                 110

Tyr Asn Phe Arg Phe Glu Ile Ser Glu Gly Asn Arg Trp Ser Asp Val
        115                 120                 125
```

-continued

```
Lys Gly Thr Val Val Thr Val Thr Glu Val Pro Ser Val Pro Thr Ile
    130                 135                 140
Ala Leu Pro Ala Lys Leu His Glu Gly Met Glu Val Asp Phe Asn Cys
145                 150                 155                 160
Ser Thr Pro Tyr Val Cys Pro Thr Glu Pro Val Asn Leu Gln Trp Gln
                    165                 170                 175
Gly Gln Asp Pro Thr Arg Ser Val Thr Ser His Leu Gln Lys Leu Glu
                180                 185                 190
Pro Ser Gly Thr Ser His Met Glu Thr Leu His Met Ala Leu Ser Trp
            195                 200                 205
Gln Asp His Gly Arg Ile Leu Ser Cys Gln Val Ser Ala Ala Glu Arg
        210                 215                 220
Arg Met Gln Lys Glu Ile His Leu Gln Val Gln Tyr Ala Pro Lys Gly
225                 230                 235                 240
Val Glu Ile Leu Phe Ser His Ser Gly Arg Asn Val Leu Pro Gly Asp
                    245                 250                 255
Leu Val Thr Leu Ser Cys Gln Val Asn Ser Ser Asn Pro Gln Val Ser
                260                 265                 270
Ser Val Gln Trp Val Lys Asp Gly Thr Lys Leu Lys Asp Gln Lys Arg
            275                 280                 285
Val Leu Gln Leu Arg Arg Ala Ala Trp Ala Asp Ala Gly Val Tyr Thr
        290                 295                 300
Cys Gln Ala Gly Asn Ala Val Gly Ser Ser Val Ser Pro Pro Val Ser
305                 310                 315                 320
Leu His Val Phe Met Ala Glu Val Gln Val Ser Pro Val Gly Ser Ile
                    325                 330                 335
Leu Glu Asn Gln Thr Val Thr Leu Ala Cys Asn Thr Pro Lys Glu Ala
                340                 345                 350
Pro Ser Glu Leu Arg Tyr Ser Trp Tyr Lys Asn His Ala Leu Leu Glu
            355                 360                 365
Gly Ser His Ser Arg Thr Leu Arg Leu His Ser Val Thr Arg Ala Asp
        370                 375                 380
Ser Gly Phe Tyr Phe Cys Glu Val Gln Asn Ala Arg Gly Arg Glu Arg
385                 390                 395                 400
Ser Pro Pro Val Ser Val Val Ser His Pro Pro Leu Thr Pro Asp
                    405                 410                 415
Leu Thr Ala Phe Leu Glu Thr Gln Ala Gly Leu Val Gly Ile Leu Gln
                420                 425                 430
Cys Ser Val Val Ser Glu Pro Pro Ala Thr Leu Val Leu Ser His Gly
            435                 440                 445
Gly Leu Ile Leu Ala Ser Thr Ser Gly Glu Gly Asp His Ser Pro Arg
        450                 455                 460
Phe Ser Val Ala Ser Ala Pro Asn Ser Leu Arg Leu Glu Ile Gln Asp
465                 470                 475                 480
Leu Gly Pro Thr Asp Ser Gly Glu Tyr Met Cys Ser Ala Ser Ser Ser
                    485                 490                 495
Leu Gly Asn Ala Ser Ser Thr Leu Asp Phe His Ala Asn Ala Ala Arg
                500                 505                 510
Leu Leu Ile Ser Pro Ala Glu Val Val Glu Gly Gln Ala Val Thr
            515                 520                 525
Leu Ser Cys Arg Ser Ser Leu Ser Leu Met Pro Asp Thr Arg Phe Ser
        530                 535                 540
Trp Tyr Leu Asn Gly Ala Leu Ile Leu Glu Gly Pro Ser Ser Ser Leu
```

```
            545                 550                 555                 560
Leu Leu Pro Ala Ala Ser Ser Thr Asp Ala Gly Ser Tyr His Cys Arg
                    565                 570                 575

Ala Gln Asn Ser His Ser Thr Ser Gly Pro Ser Pro Ala Val Leu
            580                 585                 590

Thr Val Leu Tyr Ala Pro Arg Gln Pro Val Phe Thr Ala Gln Leu Asp
        595                 600                 605

Pro Asp Thr Ala Gly Ala Gly Arg Gln Gly Leu Leu Leu Cys
    610                 615                 620

Arg Val Asp Ser Asp Pro Pro Ala Gln Leu Gln Leu Leu His Arg Gly
625                 630                 635                 640

Arg Val Val Ala Ser Ser Leu Ser Trp Gly Gly Gly Cys Cys Thr Cys
                    645                 650                 655

Gly Gly Cys Phe His Arg Met Lys Val Thr Lys Ala Pro Asn Leu Leu
            660                 665                 670

Arg Val Glu Ile Arg Asp Pro Val Leu Glu Asp Glu Gly Val Tyr Leu
        675                 680                 685

Cys Glu Ala Ser Ser Ala Leu Gly Asn Ala Ser Ala Ser Ala Thr Leu
    690                 695                 700

Asp Ala Gln Ala Thr Val Leu Val Ile Thr Pro Ser His Thr Leu Gln
705                 710                 715                 720

Glu Gly Ile Glu Ala Asn Leu Thr Cys Asn Val Ser Arg Glu Ala Ser
                    725                 730                 735

Gly Pro Ala Asn Phe Ser Trp Phe Arg Asp Gly Ala Leu Trp Ala Gln
            740                 745                 750

Gly Pro Leu Asp Thr Val Thr Leu Leu Pro Val Ala Arg Thr Asp Ala
        755                 760                 765

Ala Leu Tyr Ala Cys Arg Ile Val Thr Glu Ala Gly Ala Gly Leu Ser
    770                 775                 780

Thr Pro Val Ala Leu Asn Val Leu Tyr Pro Pro Asp Pro Pro Lys Leu
785                 790                 795                 800

Ser Ala Leu Leu Asp Val Asp Gln Gly His Thr Ala Val Phe Val Cys
                    805                 810                 815

Thr Val Asp Ser Arg Pro Leu Ala Gln Leu Ala Leu Phe Arg Gly Glu
            820                 825                 830

His Leu Leu Ala Ala Ser Ser Ala Leu Arg Leu Pro Pro Arg Gly Arg
        835                 840                 845

Leu Gln Ala Lys Ala Ser Ala Asn Ser Leu Gln Leu Glu Val Arg Asp
    850                 855                 860

Leu Ser Leu Gly Asp Ser Gly Ser Tyr His Cys Glu Ala Thr Asn Ile
865                 870                 875                 880

Leu Gly Ser Ala Asn Thr Ser Leu Thr Phe Gln Val Arg Gly Ala Trp
                    885                 890                 895

Val Arg Val Ser Pro Ser Pro Glu Leu Gln Glu Gly Gln Ala Val Val
            900                 905                 910

Leu Ser Cys Gln Val Pro Ile Gly Val Leu Glu Gly Thr Ser Tyr Arg
        915                 920                 925

Trp Tyr Arg Asp Gly Gln Pro Leu Gln Glu Ser Thr Ser Ala Thr Leu
    930                 935                 940

Arg Phe Ala Ala Ile Thr Leu Ser Gln Ala Gly Ala Tyr His Cys Gln
945                 950                 955                 960

Ala Gln Ala Pro Gly Ser Ala Thr Thr Asp Leu Ala Ala Pro Val Ser
                    965                 970                 975
```

-continued

Leu His Val Thr Tyr Ala Pro Arg Gln Ala Thr Leu Thr Thr Leu Met
                980                 985                 990

Asp Ser Gly Leu Gly Arg Leu Gly Leu Leu Cys Arg Val Asn Ser
        995                 1000                1005

Asp Pro Pro Ala Gln Leu Arg Leu Leu His Gly Ser Arg Leu Val Ala
    1010                1015                1020

Ser Thr Leu Gln Gly Val Glu Leu Ala Gly Ser Ser Pro Arg Leu
1025                1030                1035                1040

Gln Val Ala Thr Ala Pro Asn Thr Leu Arg Leu Glu Ile His Asn Ala
            1045                1050                1055

Val Leu Glu Asp Glu Gly Val Tyr Thr Cys Glu Ala Thr Asn Thr Leu
        1060                1065                1070

Gly Gln Thr Leu Ala Ser Ala Ala Phe Asp Ala Gln Ala Met Arg Val
            1075                1080                1085

Gln Val Trp Pro Asn Ala Thr Val Gln Glu Gly Gln Leu Val Asn Leu
        1090                1095                1100

Thr Cys Leu Val Trp Thr Thr His Leu Ala Gln Leu Thr Tyr Thr Trp
1105                1110                1115                1120

Tyr Arg Asp Gln Gln Gln Leu Pro Gly Ala Ala His Ser Ile Leu Leu
            1125                1130                1135

Pro Asn Val Thr Val Thr Asp Ala Ala Ser Tyr Arg Cys Gly Ile Leu
        1140                1145                1150

Ile Pro Gly Gln Ala Leu Arg Leu Ser Arg Pro Val Ala Leu Asp Val
        1155                1160                1165

Leu Tyr Ala Pro Arg Arg Leu Arg Leu Thr His Leu Leu Glu Ser Arg
    1170                1175                1180

Gly Gly Gln Leu Ala Val Val Leu Cys Thr Val Asp Ser Arg Pro Ala
1185                1190                1195                1200

Ala Gln Leu Thr Leu Ser His Ala Gly Arg Leu Leu Ala Ser Ser Thr
        1205                1210                1215

Ala Ala Ser Val Pro Asn Thr Leu Arg Leu Glu Leu Trp Glu Pro Arg
        1220                1225                1230

Pro Ser Asp Glu Gly Leu Tyr Ser Cys Ser Ala Arg Ser Pro Leu Gly
    1235                1240                1245

Gln Ala Asn Thr Ser Leu Glu Leu Arg Leu Glu Gly Val Gln Val Ala
        1250                1255                1260

Leu Ala Pro Ser Ala Thr Val Pro Glu Gly Ala Pro Val Thr Val Thr
1265                1270                1275                1280

Cys Glu Asp Pro Ala Ala Arg Pro Pro Thr Leu Tyr Val Trp Tyr His
            1285                1290                1295

Asn Ser Arg Trp Leu Gln Glu Gly Ser Ala Ala Ser Leu Ser Phe Pro
        1300                1305                1310

Ala Ala Thr Arg Ala His Ala Gly Ala Tyr Thr Cys Gln Val Gln Asp
        1315                1320                1325

Ala Gln Gly Thr Arg Ile Ser Gln Pro Ala Ala Leu His Ile Leu Tyr
    1330                1335                1340

Ala Pro Arg Asp Ala Val Leu Ser Ser Phe Trp Asp Ser Arg Ala Ser
1345                1350                1355                1360

Pro Met Ala Val Val Gln Cys Thr Val Asp Ser Glu Pro Pro Ala Glu
        1365                1370                1375

Met Thr Leu Ser His Asp Gly Lys Val Leu Ala Thr Ser His Gly Val
    1380                1385                1390

His Gly Leu Ala Val Gly Thr Gly His Val Gln Val Ala Arg Asn Ala
    1395                1400                1405

```
Leu Gln Leu Arg Val Gln Asn Val Pro Ser Arg Asp Lys Asp Thr Tyr
    1410                1415                1420
Val Cys Met Asp Arg Asn Ser Leu Gly Ser Val Ser Thr Met Gly Gln
1425                1430                1435                1440
Leu Gln Pro Glu Gly Val His Val Ala Glu Pro Gly Leu Asp Val
                1445                1450                1455
Pro Glu Gly Thr Ala Leu Asn Leu Ser Cys Arg Leu Pro Ser Gly Pro
                1460                1465                1470
Gly His Ile Gly Asn Ser Thr Phe Ala Trp Phe Arg Asn Gly Arg Gln
                1475                1480                1485
Leu His Thr Glu Ser Val Pro Thr Leu Thr Phe Thr His Val Ala Arg
                1490                1495                1500
Ala Gln Ala Gly Leu Tyr His Cys Gln Ala Glu Leu Pro Ala Gly Ala
1505                1510                1515                1520
Ala Thr Ser Ala Pro Val Leu Leu Arg Val Leu Tyr Pro Pro Lys Thr
                1525                1530                1535
Pro Thr Met Thr Val Phe Val Glu Pro Glu Gly Gly Ile Gln Gly Ile
                1540                1545                1550
Leu Asp Cys Arg Val Asp Ser Glu Pro Leu Ala Ser Leu Thr Leu His
                1555                1560                1565
Leu Gly Ser Arg Leu Val Ala Ser Ser Gln Pro Gln Ala Ala Pro Ala
                1570                1575                1580
Lys Pro His Ile Arg Val Ser Ala Ser Pro Asn Ala Leu Arg Val Asp
1585                1590                1595                1600
Met Glu Glu Leu Lys Pro Ser Asp Gln Gly Glu Tyr Val Cys Ser Ala
                1605                1610                1615
Ser Asn Ala Leu Gly Ser Ala Ser Ala Ala Thr Tyr Phe Gly Thr Arg
                1620                1625                1630
Ala Leu His Arg Leu His Leu Phe Gln His Leu Leu Trp Phe Leu Gly
                1635                1640                1645
Leu Leu Ala Ser Leu Leu Phe Leu Leu Leu Gly Leu Gly Val Trp Tyr
                1650                1655                1660
Ala Trp Arg Arg Gly Asn Phe Tyr Lys Leu Arg Met Gly Glu Tyr Ser
1665                1670                1675                1680
Val Glu Met Val Ser Arg Lys Glu Thr Thr Gln Met Ser Thr Asp Gln
                1685                1690                1695
Glu Glu Val Thr Gly Ile Gly Asp Asp Ala Gly Ser Val Asn Gln Ala
                1700                1705                1710
Ala Phe Asp Pro Ala His Leu Cys Glu Asn Thr Gln Ser Val Lys Ser
                1715                1720                1725
Thr Val
    1730

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide

<400> SEQUENCE: 5
caccatggac ttcctgctcc tgctcctc                                     28

<210> SEQ ID NO 6
<211> LENGTH: 25
<212> TYPE: DNA
```

```
<213> ORGANISM: Artificial Sequence
<220> FEATURE:
<223> OTHER INFORMATION: Oligonucleotide

<400> SEQUENCE: 6
cttggggttt gaagctaggt cataa                                              25
```